(12) United States Patent
Northey (10) Patent No.: US 10,342,825 B2
(45) Date of Patent: Jul. 9, 2019

(54) SOLUTION CONTAINING HYPOCHLOROUS ACID AND METHODS OF USING SAME

(75) Inventor: Robert Northey, Bellevue, WA (US)

(73) Assignee: Sonoma Pharmaceuticals, Inc., Petaluma, CA (US)

( * ) Notice: Subject to any disclaimer, the term of this patent is extended or adjusted under 35 U.S.C. 154(b) by 0 days.

(21) Appl. No.: 13/378,659

(22) PCT Filed: Jun. 15, 2010

(86) PCT No.: PCT/US2010/038697
§ 371 (c)(1),
(2), (4) Date: Jul. 10, 2012

(87) PCT Pub. No.: WO2010/148004
PCT Pub. Date: Dec. 23, 2010

(65) Prior Publication Data
US 2012/0269904 A1 Oct. 25, 2012

Related U.S. Application Data

(60) Provisional application No. 61/268,764, filed on Jun. 15, 2009.

(51) Int. Cl.
| | | |
|---|---|---|
| A61K 33/20 | (2006.01) | |
| A01N 59/00 | (2006.01) | |
| A61K 9/06 | (2006.01) | |
| A61K 9/12 | (2006.01) | |
| A61K 33/00 | (2006.01) | |
| A01P 1/00 | (2006.01) | |
| A61P 31/10 | (2006.01) | |
| A61P 31/00 | (2006.01) | |
| A61P 17/02 | (2006.01) | |
| A61P 31/12 | (2006.01) | |
| A61P 31/04 | (2006.01) | |
| A61P 17/00 | (2006.01) | |

(52) U.S. Cl.
CPC .............. *A61K 33/20* (2013.01); *A01N 59/00* (2013.01); *A61K 9/06* (2013.01); *A61K 9/12* (2013.01); *Y02A 50/473* (2018.01)

(58) Field of Classification Search
CPC .................................................... A01N 59/00
See application file for complete search history.

(56) References Cited

U.S. PATENT DOCUMENTS

| | | |
|---|---|---|
| 3,066,095 A | 11/1962 | Hronas |
| 3,843,548 A | 10/1974 | James |
| 3,949,742 A | 4/1976 | Nowakowski |
| 3,975,246 A | 8/1976 | Eibl et al. |
| 3,975,247 A | 8/1976 | Straiser |
| 4,048,032 A | 9/1977 | Eibl |
| 4,121,991 A | 10/1978 | Miller et al. |
| 4,146,578 A | 3/1979 | Brennan et al. |
| 4,190,638 A | 2/1980 | Hoekje et al. |
| 4,236,992 A | 12/1980 | Themy |
| 4,242,446 A | 12/1980 | Madappally et al. |
| 4,289,599 A | 9/1981 | Fushihara |
| 4,296,103 A | 10/1981 | Laso |
| 4,382,441 A | 5/1983 | Svedman |
| 4,615,937 A | 10/1986 | Bouchette |
| 4,666,621 A | 5/1987 | Clark et al. |
| 4,670,252 A | 6/1987 | Sampathkumar |
| 4,693,832 A † | 9/1987 | Hurst |
| 4,767,511 A | 8/1988 | Aragon |
| 4,781,974 A | 11/1988 | Bouchette et al. |
| 4,839,004 A | 6/1989 | Castellini |
| 4,970,216 A | 11/1990 | Deckner et al. |
| 4,979,938 A | 12/1990 | Stephen et al. |
| 5,037,627 A | 8/1991 | Melton et al. |
| 5,063,922 A | 11/1991 | Hakkinen |
| 5,079,010 A | 1/1992 | Natterer et al. |
| 5,084,011 A | 1/1992 | Grady |
| 5,126,057 A | 6/1992 | Worley et al. |
| 5,128,136 A | 7/1992 | Bentley et al. |
| 5,152,757 A | 10/1992 | Eriksson |
| 5,152,915 A | 10/1992 | Ralston, Jr. et al. |
| 5,165,910 A | 11/1992 | Oikawa et al. |
| 5,244,768 A | 9/1993 | Inaba |
| 5,271,943 A | 12/1993 | Bogart et al. |
| 5,287,847 A | 2/1994 | Piper et al. |
| 5,312,281 A | 5/1994 | Takahashi et al. |
| 5,334,383 A | 8/1994 | Morrow |
| 5,376,242 A | 12/1994 | Hayakawa |
| 5,388,571 A | 2/1995 | Roberts et al. |
| 5,427,667 A | 6/1995 | Bakhir et al. |
| 5,445,722 A | 8/1995 | Yamaguti et al. |
| 5,449,442 A | 9/1995 | Yamada et al. |
| 5,474,662 A | 12/1995 | Miyamae |
| 5,507,932 A | 4/1996 | Robinson |
| 5,510,009 A | 4/1996 | Arai et al. |
| 5,543,030 A | 8/1996 | Shiramizu et al. |
| 5,545,374 A | 8/1996 | French et al. |
| 5,560,816 A | 10/1996 | Robinson |
| 5,578,022 A | 11/1996 | Scherson et al. |

(Continued)

FOREIGN PATENT DOCUMENTS

| | | |
|---|---|---|
| CN | 1 231 994 A | 10/1999 |
| CN | 1 487 835 A | 4/2004 |

(Continued)

OTHER PUBLICATIONS

SMARTe.org (2008) http://www.smarte.org/smarte/dynamic/resource/sn-units-of-measure.xml.pdf.*

(Continued)

*Primary Examiner* — David J Blanchard
*Assistant Examiner* — Sarah Alawadi
(74) *Attorney, Agent, or Firm* — Leydig, Voit & Mayer, Ltd.

(57) ABSTRACT

The present invention relates to low pH antimicrobial solutions comprising hypochlorous acid, water, and, optionally, a buffer. The inventive low pH antimicrobial solutions have a pH from about 4 to about 6 and are useful for treating impaired or damaged tissue and for disinfecting surfaces. Chemical processes for the production of the low pH antimicrobial solutions are also provided wherein chlorine gas is added to a buffer solution containing a buffering agent and water. The present invention also provides an electrochemical process for the production of the low pH antimicrobial solutions.

6 Claims, 2 Drawing Sheets

(56) References Cited

U.S. PATENT DOCUMENTS

| | | | |
|---|---|---|---|
| 5,593,554 A | 1/1997 | Yamanaka et al. |
| 5,599,438 A | 2/1997 | Shiramizu et al. |
| 5,615,764 A | 4/1997 | Satoh |
| 5,616,221 A | 4/1997 | Aoki et al. |
| 5,620,587 A | 4/1997 | Nakamura |
| 5,622,725 A | 4/1997 | Kross |
| 5,622,848 A | 4/1997 | Morrow |
| 5,624,535 A | 4/1997 | Tsuchikawa et al. |
| 5,624,544 A | 4/1997 | Deguchi et al. |
| 5,628,888 A | 5/1997 | Bakhir et al. |
| 5,635,040 A | 6/1997 | Bakhir et al. |
| 5,635,053 A | 6/1997 | Aoki et al. |
| 5,636,643 A | 6/1997 | Argenta et al. |
| 5,662,625 A | 9/1997 | Westwood |
| 5,674,365 A | 10/1997 | Sano |
| 5,674,537 A | 10/1997 | Morrow |
| 5,720,869 A | 2/1998 | Yamanaka et al. |
| 5,728,274 A | 3/1998 | Kamitani et al. |
| 5,728,287 A | 3/1998 | Hough et al. |
| 5,731,008 A | 3/1998 | Morrow |
| 5,736,027 A | 4/1998 | Nakamura |
| 5,759,489 A | 6/1998 | Miura et al. |
| 5,762,779 A | 6/1998 | Shiramizu et al. |
| 5,783,052 A | 7/1998 | Bakhir et al. |
| 5,792,090 A | 8/1998 | Ladin |
| 5,798,028 A | 8/1998 | Tsuchikawa et al. |
| 5,833,831 A | 11/1998 | Kitajima et al. |
| 5,843,291 A | 12/1998 | Eki et al. |
| 5,858,201 A | 1/1999 | Otsuka et al. |
| 5,858,202 A | 1/1999 | Nakamura |
| 5,871,623 A | 2/1999 | Dakhir et al. |
| 5,888,357 A | 3/1999 | Mitsumori et al. |
| 5,888,528 A | 3/1999 | Wellinghoff et al. |
| 5,897,757 A | 4/1999 | Sano |
| 5,900,257 A | 5/1999 | Breton et al. |
| 5,902,619 A | 5/1999 | Rubow et al. |
| 5,906,810 A | 5/1999 | Turner |
| 5,908,707 A | 6/1999 | Cabell et al. |
| 5,928,488 A | 7/1999 | Newman |
| 5,928,491 A | 7/1999 | Yu et al. |
| 5,932,171 A | 8/1999 | Malchesky |
| 5,938,915 A | 8/1999 | Morisawa |
| 5,938,916 A | 8/1999 | Bryson et al. |
| 5,941,859 A | 8/1999 | Lerman |
| 5,944,978 A | 8/1999 | Okazaki |
| 5,948,220 A | 9/1999 | Kamitani et al. |
| 5,951,859 A | 9/1999 | Mirua et al. |
| 5,963,435 A | 10/1999 | Biernson |
| 5,964,089 A | 10/1999 | Murphy et al. |
| 5,965,009 A | 10/1999 | Shimamune et al. |
| 5,980,703 A | 11/1999 | Yamada et al. |
| 5,985,110 A | 11/1999 | Bakhir et al. |
| 5,993,639 A | 11/1999 | Miyashita et al. |
| 5,997,717 A | 12/1999 | Miyashita et al. |
| 6,007,686 A | 12/1999 | Welch et al. |
| 6,007,693 A | 12/1999 | Silveri |
| 6,007,696 A | 12/1999 | Takayasu et al. |
| 6,033,539 A | 3/2000 | Gablenko |
| 6,056,866 A | 5/2000 | Maeda et al. |
| 6,059,941 A | 5/2000 | Bryson et al. |
| 6,093,292 A | 7/2000 | Akiyama |
| 6,106,691 A | 8/2000 | Nakamura et al. |
| 6,117,285 A | 9/2000 | Welch et al. |
| 6,121,317 A | 9/2000 | Wu et al. |
| 6,126,796 A | 10/2000 | Shimamune et al. |
| 6,126,810 A | 10/2000 | Fricker et al. |
| 6,139,876 A | 10/2000 | Kolta |
| 6,143,163 A | 11/2000 | Sawamoto et al. |
| 6,149,780 A | 11/2000 | Miyake |
| 6,171,551 B1 | 1/2001 | Malchesky et al. |
| 6,174,419 B1 | 1/2001 | Akiyama |
| 6,187,154 B1 | 2/2001 | Yamaguchi et al. |
| 6,197,814 B1 | 3/2001 | Arata et al. |
| 6,200,434 B1 | 3/2001 | Shinjo et al. |
| 6,210,748 B1 | 4/2001 | Nagahara et al. |
| 6,228,251 B1 | 5/2001 | Okazaki |
| 6,231,747 B1 | 5/2001 | Fukuzuka et al. |
| 6,231,878 B1 | 5/2001 | Komatsu et al. |
| 6,245,210 B1 | 6/2001 | Nakamura et al. |
| 6,251,259 B1 | 6/2001 | Satoh et al. |
| 6,258,225 B1 | 7/2001 | Yamaoka |
| 6,277,266 B1 | 8/2001 | Yamaoka |
| 6,280,594 B1 | 8/2001 | Yamaoka |
| 6,294,073 B1 | 9/2001 | Shirota et al. |
| 6,296,744 B1 | 10/2001 | Djeiranishvili et al. |
| 6,333,054 B1 | 12/2001 | Rogozinski |
| 6,340,663 B1 | 1/2002 | Deleo et al. |
| 6,342,150 B1 | 1/2002 | Sale et al. |
| 6,350,376 B1 | 2/2002 | Imaoka et al. |
| 6,358,395 B1 | 3/2002 | Schorzman et al. |
| 6,361,665 B1 | 3/2002 | Vorack |
| 6,368,592 B1 | 4/2002 | Colton et al. |
| 6,375,809 B1 | 4/2002 | Kato et al. |
| 6,384,363 B1 | 5/2002 | Hayakawa et al. |
| 6,391,169 B1 | 5/2002 | Hara et al. |
| 6,426,066 B1 | 7/2002 | Najafi et al. |
| 6,436,445 B1 | 8/2002 | Hei et al. |
| 6,444,255 B2 | 9/2002 | Nagahara et al. |
| 6,462,250 B1 | 10/2002 | Kuriyama et al. |
| 6,464,845 B2 | 10/2002 | Shirota et al. |
| 6,475,371 B1 | 11/2002 | Shirahata et al. |
| 6,506,416 B1 | 1/2003 | Oakauchi et al. |
| 6,527,940 B1 | 3/2003 | Shimamune et al. |
| 6,544,502 B2 | 4/2003 | Heesch |
| 6,551,492 B2 | 4/2003 | Hanaoka |
| 6,558,620 B1 * | 5/2003 | Sanford ............... A61B 1/123 134/102.2 |
| 6,565,736 B2 | 5/2003 | Park et al. |
| 6,585,867 B1 | 7/2003 | Asano |
| 6,585,868 B1 | 7/2003 | Chihara |
| 6,598,602 B1 | 7/2003 | Sjoholm |
| 6,620,315 B2 | 9/2003 | Martin |
| 6,623,615 B1 | 9/2003 | Morisawa et al. |
| 6,623,695 B2 | 9/2003 | Malchesky et al. |
| 6,624,135 B2 | 9/2003 | Takano |
| 6,632,347 B1 | 10/2003 | Buckley et al. |
| 6,638,364 B2 | 10/2003 | Harkins et al. |
| 6,638,413 B1 | 10/2003 | Weinberg et al. |
| 6,663,306 B2 | 12/2003 | Policicchio et al. |
| 6,716,335 B2 | 4/2004 | Takesako et al. |
| 6,723,226 B1 | 4/2004 | Takayasu et al. |
| 6,733,435 B2 | 5/2004 | Canedo |
| 6,743,351 B1 | 6/2004 | Arai et al. |
| 6,752,757 B2 | 6/2004 | Muir et al. |
| 6,767,342 B1 | 7/2004 | Cantwell |
| 6,793,846 B2 | 9/2004 | Yoshikawa et al. |
| 6,815,551 B2 | 11/2004 | Albiez et al. |
| 6,823,609 B2 | 11/2004 | Moretti |
| 6,827,849 B2 | 12/2004 | Kurokawa et al. |
| 6,833,206 B2 | 12/2004 | Erdle et al. |
| 6,833,207 B2 | 12/2004 | Joos et al. |
| 6,838,210 B2 | 1/2005 | Sawa |
| 6,843,448 B2 | 1/2005 | Parmley |
| 6,844,026 B2 | 1/2005 | Anthony et al. |
| 6,852,205 B1 | 2/2005 | Toyoshima et al. |
| 6,855,233 B2 | 2/2005 | Sawada |
| 6,855,307 B2 † | 2/2005 | Shane |
| 6,855,490 B2 | 2/2005 | Sompuram et al. |
| 6,856,916 B2 | 2/2005 | Shyu |
| 6,866,756 B2 | 3/2005 | Klein |
| 6,867,048 B2 | 3/2005 | Kovacs |
| 6,874,675 B2 | 4/2005 | Kida et al. |
| 6,887,601 B2 | 5/2005 | Moulthrop et al. |
| 6,899,903 B2 | 5/2005 | Quillin |
| 6,921,743 B2 | 7/2005 | Scheder et al. |
| 6,923,893 B2 | 8/2005 | Sano |
| 7,276,051 B1 | 10/2007 | Henley et al. |
| 7,276,255 B2 | 10/2007 | Selkon |
| 7,393,522 B2 | 7/2008 | Najafi et al. |
| 7,749,370 B2 | 7/2010 | Sumita |
| 7,758,807 B2 | 7/2010 | Smith et al. |
| 8,147,444 B2 | 4/2012 | Alimi et al. |
| 2001/0012544 A1 | 8/2001 | Nagahara et al. |
| 2001/0022273 A1 | 9/2001 | Popov et al. |

(56) References Cited

U.S. PATENT DOCUMENTS

| | | |
|---|---|---|
| 2002/0006961 A1 | 1/2002 | Katz et al. |
| 2002/0023847 A1 | 2/2002 | Natsume |
| 2002/0027070 A1 | 3/2002 | Oyokota et al. |
| 2002/0027079 A1 | 3/2002 | Hanaoka |
| 2002/0027084 A1 | 3/2002 | Park et al. |
| 2002/0032141 A1 | 3/2002 | Harkins |
| 2002/0036134 A1 | 3/2002 | Shirota et al. |
| 2002/0064565 A1 | 5/2002 | Karagoezian |
| 2002/0074237 A1 | 6/2002 | Takesako et al. |
| 2002/0082196 A1 | 6/2002 | Zaveri |
| 2002/0112314 A1 | 8/2002 | Harkins |
| 2002/0134691 A1 | 9/2002 | Satoh et al. |
| 2002/0135220 A1 | 9/2002 | Yamaguchi et al. |
| 2002/0160053 A1 | 10/2002 | Yahagi et al. |
| 2002/0165220 A1 | 11/2002 | Heesch |
| 2002/0165431 A1 | 11/2002 | Muir et al. |
| 2002/0168418 A1 | 11/2002 | Lorenz et al. |
| 2002/0175085 A1 | 11/2002 | Harkins et al. |
| 2002/0176885 A1 | 11/2002 | Najafi et al. |
| 2002/0179884 A1 | 12/2002 | Hoshino et al. |
| 2002/0182262 A1 | 12/2002 | Selkon |
| 2003/0015418 A1 | 1/2003 | Tseng et al. |
| 2003/0019764 A1 | 1/2003 | Baldwin et al. |
| 2003/0024828 A1 | 2/2003 | Kondo et al. |
| 2003/0045502 A1 | 3/2003 | Kataoka et al. |
| 2003/0049163 A1 | 3/2003 | Malchesky et al. |
| 2003/0056805 A1 | 3/2003 | Sumita |
| 2003/0062068 A1 | 4/2003 | Ko et al. |
| 2003/0064427 A1 | 4/2003 | Felkner et al. |
| 2003/0087427 A1 | 5/2003 | Colton et al. |
| 2003/0089618 A1 | 5/2003 | Satoh et al. |
| 2003/0098283 A1 | 5/2003 | Katayose et al. |
| 2003/0138496 A1 | 7/2003 | Yoshikawa et al. |
| 2003/0141200 A1 | 7/2003 | Harada |
| 2003/0155549 A1 | 8/2003 | Yoshikawa et al. |
| 2003/0175220 A1 | 9/2003 | Wang et al. |
| 2003/0185704 A1 | 10/2003 | Bernard et al. |
| 2003/0212005 A1 | 11/2003 | Petito et al. |
| 2003/0219361 A1 | 11/2003 | Lee et al. |
| 2003/0230826 A1 | 12/2003 | Kawaguchi et al. |
| 2004/0004007 A1 | 1/2004 | Orolin et al. |
| 2004/0011665 A1 | 1/2004 | Koizumi et al. |
| 2004/0029761 A1 | 2/2004 | Wakamatsu et al. |
| 2004/0037737 A1 | 2/2004 | Marais et al. |
| 2004/0055896 A1 | 3/2004 | Anderson et al. |
| 2004/0060815 A1 | 4/2004 | Buckley et al. |
| 2004/0062818 A1 | 4/2004 | Calderon |
| 2004/0079791 A1 | 4/2004 | Kida et al. |
| 2004/0081705 A1 | 4/2004 | Gotou |
| 2004/0084325 A1 | 5/2004 | Weinberg et al. |
| 2004/0084326 A1 | 5/2004 | Weinberg et al. |
| 2004/0094406 A1 | 5/2004 | Sawada |
| 2004/0131695 A1 | 7/2004 | Hinze |
| 2004/0137078 A1 | 7/2004 | Najafi et al. |
| 2004/0154993 A1 | 8/2004 | Yanagihara et al. |
| 2004/0168909 A1 | 9/2004 | Larson |
| 2004/0168933 A1 | 9/2004 | Inoue |
| 2004/0171701 A1 | 9/2004 | Shaw |
| 2004/0172985 A1 | 9/2004 | Mamiya et al. |
| 2004/0177655 A1 | 9/2004 | Kodera et al. |
| 2004/0185311 A1 | 9/2004 | Muthuswamy et al. |
| 2004/0185313 A1 | 9/2004 | Halter et al. |
| 2004/0188248 A1 | 9/2004 | Sawa |
| 2004/0208940 A1 | 10/2004 | Selkon |
| 2004/0226894 A1 | 11/2004 | Okazaki |
| 2004/0231977 A1 | 11/2004 | Roselle et al. |
| 2004/0244537 A1 | 12/2004 | Runyon |
| 2004/0250323 A1 | 12/2004 | Arai et al. |
| 2004/0254744 A1 | 12/2004 | Shyu |
| 2004/0256317 A1 | 12/2004 | Yamada et al. |
| 2004/0265394 A1 | 12/2004 | Morris et al. |
| 2005/0000117 A1 | 1/2005 | Polegata Moretti |
| 2005/0054973 A1 | 3/2005 | Constantz et al. |
| 2005/0058013 A1 | 3/2005 | Warf et al. |
| 2005/0062289 A1 | 3/2005 | Cho et al. |
| 2005/0064259 A1 | 3/2005 | Coors |
| 2005/0067300 A1 | 3/2005 | Tremblay et al. |
| 2005/0074421 A1 | 4/2005 | Tanaka |
| 2005/0075257 A1 | 4/2005 | Scheper et al. |
| 2005/0101838 A1 | 5/2005 | Camillocci et al. |
| 2005/0109610 A1 | 5/2005 | Inamoto et al. |
| 2005/0121334 A1 | 6/2005 | Sumita |
| 2005/0126927 A1 | 6/2005 | Lindauer et al. |
| 2005/0126928 A1 | 6/2005 | Hung et al. |
| 2005/0129996 A1 | 6/2005 | Moulthrop et al. |
| 2005/0139465 A1 | 6/2005 | Kasuya et al. |
| 2005/0139808 A1 | 6/2005 | Alimi |
| 2005/0142157 A1 | 6/2005 | Alimi |
| 2005/0153858 A1 | 7/2005 | Anthony et al. |
| 2005/0155863 A1 | 7/2005 | Kovacs et al. |
| 2005/0161950 A1 | 7/2005 | Borden et al. |
| 2005/0178349 A1 | 7/2005 | Tse |
| 2005/0178920 A1 | 8/2005 | Wilson |
| 2005/0180925 A1 | 8/2005 | Chaudry |
| 2005/0183949 A1 | 8/2005 | Daly et al. |
| 2005/0183964 A1 | 8/2005 | Roberts et al. |
| 2005/0189234 A1 | 9/2005 | Gibson et al. |
| 2005/0189237 A1 | 9/2005 | Sano |
| 2005/0191372 A1 | 9/2005 | Stenzler et al. |
| 2005/0196462 A1 | 9/2005 | Alimi |
| 2005/0198963 A1 | 9/2005 | Wai et al. |
| 2005/0209518 A1 | 9/2005 | Sage et al. |
| 2005/0228046 A1 | 10/2005 | Yu |
| 2006/0086622 A1 | 4/2006 | Prior |
| 2006/0163085 A1 | 7/2006 | Hanaoka |
| 2006/0169575 A1† | 8/2006 | Sumita |
| 2006/0235350 A1 | 10/2006 | Alimi et al. |
| 2006/0241002 A1 | 10/2006 | Rogozinski |
| 2006/0253060 A1 | 11/2006 | Alimi |
| 2006/0263240 A1 | 11/2006 | Hopkins |
| 2006/0275498 A1 | 12/2006 | Bagley |
| 2007/0118096 A1 | 5/2007 | Smith et al. |
| 2007/0148256 A1 | 6/2007 | Yanagihara et al. |
| 2007/0196357 A1 | 8/2007 | Alimi et al. |
| 2007/0196434 A1 | 8/2007 | Alimi et al. |
| 2007/0231247 A1* | 10/2007 | Bromberg et al. ......... 423/473 |
| 2007/0265586 A1 | 11/2007 | Joshi et al. |
| 2008/0125494 A1 | 5/2008 | Yu |
| 2008/0160612 A1 | 7/2008 | Selkon |
| 2008/0193423 A1 | 8/2008 | Brunton et al. |
| 2008/0215019 A1 | 9/2008 | Malamutmann |
| 2008/0279963 A1 | 11/2008 | Najafi et al. |
| 2009/0068255 A1 | 3/2009 | Yu et al. |
| 2012/0164235 A1 | 6/2012 | Northey et al. |
| 2012/0251631 A1 | 10/2012 | Alimi et al. |

FOREIGN PATENT DOCUMENTS

| | | |
|---|---|---|
| CN | 1 938 053 A | 3/2007 |
| CN | 101163491 A | 4/2008 |
| CN | 101189017 A | 5/2008 |
| DE | 30 46 324 A1 | 12/1982 |
| DE | 10 2004 056456 A1 | 5/2006 |
| EP | 0 368 812 A1 | 5/1990 |
| EP | 0 601 891 A1 | 6/1994 |
| EP | 0 636 581 A1 | 7/1994 |
| EP | 0 740 329 A1 | 10/1996 |
| EP | 0 826 636 A1 | 3/1998 |
| EP | 0 841 305 A2 | 5/1998 |
| EP | 0 889 007 A1 | 1/1999 |
| EP | 0 949 205 A1 | 10/1999 |
| EP | 1 038 993 A1 | 9/2000 |
| EP | 1 064 845 A1 | 1/2001 |
| EP | 1 065 265 A1 | 1/2001 |
| EP | 1 074 515 A2 | 2/2001 |
| EP | 1 103 264 A2 | 5/2001 |
| EP | 1 162 176 A1 | 12/2001 |
| EP | 1 162 179 A1 | 12/2001 |
| EP | 1 293 481 A2 | 3/2003 |
| EP | 1 314 699 A1 | 5/2003 |
| EP | 1 386 887 A1 | 2/2004 |
| EP | 2 130 542 A1 | 12/2009 |
| GB | 1 422 795 A | 1/1976 |
| GB | 2253860 A | 9/1992 |

(56) References Cited

FOREIGN PATENT DOCUMENTS

| | | |
|---|---|---|
| GB | 2352728 A | 2/2001 |
| JP | 01-194993 A | 8/1989 |
| JP | 01-218682 A | 8/1989 |
| JP | 02-149395 A | 6/1990 |
| JP | 05-228474 A | 9/1993 |
| JP | 05-228475 A | 9/1993 |
| JP | 05-339769 A | 12/1993 |
| JP | 06-182345 A | 7/1994 |
| JP | 06-254567 A | 9/1994 |
| JP | 06-312183 A | 11/1994 |
| JP | 06-335685 A | 12/1994 |
| JP | 07-000966 A | 1/1995 |
| JP | 07-010762 A | 1/1995 |
| JP | 07-031981 A | 2/1995 |
| JP | 07-075784 A | 3/1995 |
| JP | 07-155760 A | 6/1995 |
| JP | 07-214063 A | 8/1995 |
| JP | 07-323289 A | 12/1995 |
| JP | 07-328640 A | 12/1995 |
| JP | 08-001160 A | 1/1996 |
| JP | 08-052476 A | 2/1996 |
| JP | 08-061788 A | 3/1996 |
| JP | 08-164192 A | 6/1996 |
| JP | 08-326124 A | 12/1996 |
| JP | 09-025236 A | 1/1997 |
| JP | 09-157173 A | 6/1997 |
| JP | 09-290269 A | 11/1997 |
| JP | 10-080686 A | 3/1998 |
| JP | 10-113664 A | 5/1998 |
| JP | 10-128331 A | 5/1998 |
| JP | 10-192860 A | 7/1998 |
| JP | 11-151493 A | 6/1999 |
| JP | 2000-084559 A | 3/2000 |
| JP | 2000-189972 A | 7/2000 |
| JP | 2001-079548 A | 3/2001 |
| JP | 2001-096275 A | 4/2001 |
| JP | 2001-113276 A | 4/2001 |
| JP | 2001-191076 A | 7/2001 |
| JP | 2001-286868 A | 10/2001 |
| JP | 03-236315 B2 | 12/2001 |
| JP | 03-247134 B2 | 1/2002 |
| JP | 2002-059164 A | 2/2002 |
| JP | 2002-145787 A | 5/2002 |
| JP | 03-299250 B2 | 7/2002 |
| JP | 03-338435 B2 | 10/2002 |
| JP | 2002-363017 * | 12/2002 |
| JP | 2003-40716 * | 2/2003 |
| JP | 03-396853 B2 | 4/2003 |
| JP | 2003-236543 A | 8/2003 |
| JP | 03-458341 B2 | 10/2003 |
| JP | 2004-049946 A | 2/2004 |
| JP | 2004-173628 A | 6/2004 |
| JP | 2004-216349 A | 8/2004 |
| JP | 2004-223306 A | 8/2004 |
| JP | 2004-223309 A | 8/2004 |
| JP | 2004-223310 A | 8/2004 |
| JP | 2004-232413 A | 8/2004 |
| JP | 2005-013520 A | 1/2005 |
| JP | 2005-058848 A | 3/2005 |
| RO | 117 540 B1 | 4/2002 |
| SU | 1296156 A1 | 3/1987 |
| WO | WO 95/01137 A1 | 1/1995 |
| WO | WO 96/02271 A1 | 2/1996 |
| WO | WO 96/14835 A1 | 5/1996 |
| WO | WO 96/16555 A1 | 6/1996 |
| WO | WO 97/40814 A1 | 11/1997 |
| WO | WO 97/46489 A1 | 12/1997 |
| WO | WO 97/49638 A | 12/1997 |
| WO | WO 98/03713 A1 | 1/1998 |
| WO | WO 98/17588 A1 | 4/1998 |
| WO | WO 98/27013 A1 | 6/1998 |
| WO | WO 98/42625 A1 | 10/1998 |
| WO | WO 98/58880 A1 | 12/1998 |
| WO | WO 99/00588 A2 | 1/1999 |
| WO | WO 99/28238 A1 | 6/1999 |
| WO | WO 00/33757 A1 | 6/2000 |
| WO | WO 00/76475 A1 | 12/2000 |
| WO | WO 01/13926 A2 | 3/2001 |
| WO | WO 01/54704 A1 | 8/2001 |
| WO | WO 01/56616 A2 | 8/2001 |
| WO | WO 02/04032 A2 | 1/2002 |
| WO | WO 03/000957 A1 | 1/2003 |
| WO | WO 03/024491 A2 | 3/2003 |
| WO | WO 03/042111 A2 | 5/2003 |
| WO | WO 03/048421 A1 | 6/2003 |
| WO | WO 03/076688 A2 | 9/2003 |
| WO | WO 2004/080901 A1 | 9/2003 |
| WO | WO 03/103522 A1 | 12/2003 |
| WO | WO 2004/076721 A2 | 9/2004 |
| WO | WO 2004/078654 A2 | 9/2004 |
| WO | WO 2004/079051 A1 | 9/2004 |
| WO | WO 2004/081222 A2 | 9/2004 |
| WO | WO 2004/081515 A2 | 9/2004 |
| WO | WO 2004/082690 A1 | 9/2004 |
| WO | WO 2004/092571 A1 | 10/2004 |
| WO | WO 2005/003848 A1 | 1/2005 |
| WO | WO 2005/009336 A2 | 2/2005 |
| WO | WO 2005/011417 A2 | 2/2005 |
| WO | WO 2005/020896 A2 | 3/2005 |
| WO | WO 2005/030651 A1 | 4/2005 |
| WO | WO 95/265383 A2 | 7/2005 |
| WO | WO 2005/061394 A1 | 7/2005 |
| WO | WO 2005/065383 A2 | 7/2005 |
| WO | WO 2005/075581 A1 | 8/2005 |
| WO | WO 2005/080639 A1 | 9/2005 |
| WO | WO 2005/082176 A1 | 9/2005 |
| WO | WO 2005/117914 A2 | 12/2005 |
| WO | WO 2006/014578 A2 | 2/2006 |
| WO | WO 2006/102680 A2 | 9/2006 |
| WO | WO 2006/102681 A2 | 9/2006 |
| WO | WO 2006/119300 A2 | 11/2006 |
| WO | WO 2007/031765 A1 | 3/2007 |
| WO | WO 2007/085018 A2 | 7/2007 |
| WO | WO 2008/043067 A2 | 4/2008 |
| WO | WO 2008/089268 A2 | 7/2008 |
| WO | WO 2008/112940 A1 | 9/2008 |

OTHER PUBLICATIONS

International Searching Authority, International search report and written opinion relative to cognate PCT international patent application No. PCT/US2010/038697, dated Dec. 29, 2011.
"Buffer Solution," Wikipedia, http://en.wikipedia.org/wiki/Buffer_solution, retrieved Sep. 16, 2011.
"New Remedies of 1917," American Journal of Pharmacy, vol. 90, p. 254 (1918).
"Sodium Hypochlorite," *Iryoyaku Nihon Iuakuhin Shu*, 2004 Edition, p. 886.
"Treatments for Cystic Fibrosis," Cystic Fibrosis Foundation, http://cystic-fibrosis.emedtv.com/cystic-fibrosis/treatment-for-cystic-fibrosis.html, retrieved Jun. 28, 2012.
Arrigo et al., "Cytotoxic effects induced by oxidative stress in culture mammalian cells and protection provided by Hsp27 expression," *Methods*, 35, 126-138 (2005).
Ash et al., "*Handbook of Cosmetic and Personal Care Additives*," Grower Publishing Limited, Hampshire, England, 1994. See, title, contents, pp. 602, 760.
Ayliffe, "Working Party Report: Decontamination of minimally invasive surgical endoscopes and accessories," *Journal of Hospital Infection*, 45, 263-277 (2000).
Badia et al., "Saline Wound Irrigation Reduces the Postoperative Infection Rate in Guinea Pigs," *Journal of Surgical Research*, 63, 457-459 (1996).
Bari et al., "Chemical and irradiation treatments for killing *Escherichia coli* O157:H7 on alfalfa, radish, and mung bean seeds," *J Food Prot.*, 66(5), 767-774 (2003).
Bari et al., "Effectiveness of electrolyzed acidic water in killing *Escherichia coli* O157:H7, *Salmonella enteritidis*, and *Listeria monocytogenes* on the surfaces of tomatoes," *J Food Prot.*, 66(4), 542-548 (2003).

(56) References Cited

OTHER PUBLICATIONS

Beckman et al., "The free radical theory of aging matures," *Physiol. Rev.* 78, 547-581 (1998).

Bibashi et al., "Fungal peritonitis Complicating peritoneal dialysis during an 11-year period: report of 46 cases," *Clinical Infectious Diseases*, 36: 927-931 (2003).

Boulton, "The Diabetic Foot," in *Diabetes: Clinical Management*, Chapter 26, 293-306 (1990).

Brook, "Bacteriology of Acute and Chronic Ethmoid Sinusitis," *Journal of Clinical Microbiology*, vol. 43, No. 7, pp. 3479-3480 (2005).

Bunyan, "The treatment of burns by hypochlorite solution," *Journal of Tropical Pediatrics*, vol. 29, No. 2, pp. 93-94 (1983).

Carlson, "Redox media as a factor in destroying germs," *Schriftenreihe des Vereins fuer Wasser-, Boden- und Lufthygiene*, 31, 21-39 (1970).

Carton et al., "Hypotonicity induces membrane protrusions and actin remodeling via activation of small GTPases Rac and Cdc42 in Rat-1 fibroblast," *Am. J. Physiol. Cell. Physiol.*, 285, C935-C944 (2003).

Chernomorskii, "Diagram of the electrochemical stability of water", *Russian Journal of Physical Chemistry*, 51(4), pp. 542-544 (1977) translation of article published in *Zhurnal Fizicheskoi Khimii*, 51, 924-925 (1977).

Chisholm, "Wound Evaluation and Cleansing," *Soft Tissue Emergencies*, 10(4), 665-672 (1992).

Cui et al., "Physicochemical properties and bactericidal efficiency of neutral and acidic electrolyzed water under different storage conditions," *Journal of Food Engineering*, No. 91, pp. 582-586 (2009).

De Beer et al., "Direct Measurement of Chlorine Penetration into Biofilms during Disinfection," *Applied and Environmental Microbiology*, vol. 60, No. 12, pp. 4339-4344 (1994).

De Grey, "Reactive oxygen species production in the mitochondrial matrix: implications for the mechanism of mitochondrial mutation accumulation," *Rejuvenation Res.*, 8(1), 13-17 (2005).

De Lloyd, "Parts Per Millions Conversions," *Delloyd's Lab Tech Resources Reagents and Solutions*, http://delloyd.50megs.com/ppm.html (2000), downloaded Feb. 13, 2013.

Dimri et al., "A biomarker that identifies senescent human cell in culture and in aging skin in vivo," *Proc. Natl. Acad. Sci. USA*, 92(20), 9363-9667 (1995).

Dire et al., "A Comparison of Wound Irrigation Solutions Used in the Emergency Department," *Ann Emerg Med.*, 19(6), 704-708 (1998).

Dressler et al., "Controls, Standards, and Histogram Interpretation in DNA Flow Cytometry," *Methods in Cell Biology*, 41, Chpt 17, pp. 241-262 (1994).

Dyson et al., "Comparison of the Effects of Moist and Dry Conditions on Dermal Repair," *Journal for Investigative Dermatology*, 91(5), 434-439 (1988).

Erwin-Toth et al., "Wound Care Selecting the Right Dressing," *Am J Nurs.*, 95(2), 46-51 (1995).

Eventov et al., "Detoxication and Disinfection with Sodium Hypochlorite," *Biomedical Engineering*, vol. 32, No. 6 (1998).

Fabrizio et al., "Comparison of electrolyzed oxidizing water with various antimicrobial interventions to reduce *Salmonella* species on poultry," *Poultry Science*, 81(10), pp. 1598-1605 (2002).

Field et al., "Overview of Wound Healing in a Moist Environment," *Am J Surg.*, 167(1A), 2S-6S (1994).

Flint et al., "Virus cultivation, detection and genetics," in Principles of Virology, Molecular Biology, Pathogenesis and Control, Chapter 2, 25-56 (ASM Press 2000).

Fomin et al., "Participation of water [hydroxyl ions] in oxidation-reduction processes," *Sostoyanie Rol Vody Biol. Ob'ektakh, Simp., Tiflis*, 120-131 (1967) (Abstract only).

Fraga et al., "Ascorbic acid protects against endogenous oxidative DNA damage in human sperm," *Proc. Natl. Acad. Sci USA*, 88(24), 11003-11006 (1991).

Fraise, "Choosing disinfectants," *J Hosp infect*, 43, 255-264 (1999).

Frantz, "In Vivo We Trust," *Nature Reviews Drug Discovery*, No. 2, p. 501 (2003).

Free Dictionary.com, "Normal Saline" definition, retrieved from http://medical-dictionary.thefreedictionary.com/normal+saline on May 4, 2011.

Frippiat et al., "Subcytotoxic H2O2 stress triggers a release of transforming growth factor-beta, which induces biomarkers of cellular senescence of human diploie fibroblast," *J. Biol. Chem.* 276, 2531-2537 (2001).

Gao et al., "Observation on the effect of disinfection to HBsAg by electrolyzed oxidizing water," *Chinese Journal of Epidemiology*, 22(1), pp. 40-42 (2001).

Goberdham et al., "A biomarker that identifies senescent human cell in culture and in aging skin in vivo," *Proc. Natl. Acad. Sci. USA*, 92, 9663-9667 (1995).

Guitierrez et al., "Produccion de agents biologicos par alas terapias genicas y celulares en humanos," *Diagnostico molecular en medicina*, 265-291 (2003).

Harada, "Behavior of hydrogen peroxide in electrolyzed anode water," *Biosci. Biotechnol Biochem.*, 66(9), 1783-1791 (2002).

Hatto et al., "The physiological property and function of the electrolyzed-ionized calcium Aquamax on water molecular clusters fractionization," *Artif. Organs*, 21(1), 43-49 (1997). (Abstract only).

Hayashi et al., "Successful treatment of mediastinitis after cardiovascular surgery using electrolyzed strong acid water aqueous solution," *Artif Organs*, 21, 39-42 (1997).

Higgins et al., "Wound dressings and Topical Agents," *The Diabetic Foot*, 12(1), 31-40, (1995).

Hinman et al., "Effect of Air Exposure and Occlusion on Experimental Human Skin Wounds," *Nature*, 200, No. 4904, 377-379 (1963).

Hollander et al., "Laceration Management," *Annals of Emergency Medicine*, 34(3), 356-367 (1999).

Holmes et al., "Interactions of *Candida albicans* with bacteria and salivary molecules in oral biofilms," *Journal of Industrial Microbiology*, vol. 15, pp. 208-213 (1995).

Horiba et al., "Bactericidal effect of electrolyzed neutral water on bacteria isolated from infected root canals," *Oral Surg Oral Med Oral Pathol Oral Radiol Endod*, 87(1), 83-87 (1999).

Horita et al., "Healing of Fournier's gangrene of the scrotum in a haemodialysis patient after conservative therapy alone," *Nephrology Dialysis Transplantation*, 15(3): 419-421 (2000).

Hybrid Turkeys, "Effective Chlorination" Info Sheet (3 pgs.) no date.

Inoue et al., "Trial of electrolyzed strong acid aqueous solution lavage in the treatment of peritonitis and intraperitoneal abscess," *Artif Organs*, 21(1), 28-31 (1997).

Ivanova et al., "Mechanism of the extracellular antioxidant defend," *Experimental Pathology and Parasitology*, 4, 49-59 (2000).

Iwasawa et al., "Bactericidal effect of acidic electrolyzed water—comparison of chemical acidic sodium hydrochloride (NaOCl) solution," *Kansenshogaku Zasshi—Journal of Japanese Association on Infectious Diseases*, 70(9), 915-922 (1996) Abstract only.

Iwasawa et al., "The influence of pH on bactericidal effects of strong acidic electrolyzed water," *Bokin Bobai*, 30(10), 635-643, (2002).

Jeter et al., "Wound Dressings of the Nineties: Indications and Contraindications," *Wound Healing*, 8(4), 799-816 (1991).

Jiang et al., "5-Chlorouracil, A Marker of DNA Damage from Hypochlorous Acid during Inflammation," *Journal of Biological Chemistry*, vol. 278, No. 35, pp. 32834-32840 (2003).

Kanofsky et al., "Singlet Oxygen Production by Chloroperoxidase-Hydrogen Peroxide-Halide Systems," *Journal of Biological Chemistry*, vol. 259, No. 9, pp. 5596-5600 (1984).

Kanofsky et al., "Singlet Oxygen Production from the Reactions of Ozone with Biological Molecules," *Journal of Biological Chemistry*, vol. 266, No. 4, pp. 9039-9042 (1991).

Kaufman et al., "Preventing Diabetic Foot Ulcers," *Derm. Nurs.*, 6(5), 313-320 (1994).

Kim et al., "Efficacy of electrolyzed oxidizing water in inactivating *Salmonella* on alfalfa seeds and sprouts," *J Food Prot.*, 66(2), 208-214 (2003).

(56) References Cited

OTHER PUBLICATIONS

Kim et al., "Roles of oxidation-reduction potential in electrolyzed oxidizing and chemically modified water for the inactivation of food-related pathogens," *J Food Prot*, 63, 19-24 (2000).
Kimbrough et al., "Electrochemical removal of bromide and reduction of THM formation potential in drinking water," *Water Res.*, 36(19), 4902-4906 (2002).
Kitamoto et al., "Use of hyperacidity water in hemodialysis facilities," *Journal of Osaka Society for Dialysis Treatment*, vol. 15, No. 2, pp. 183-186 (1997).
Kitaoka, K., "On the electrolytic separation factor of tritium," *Radioisotopes*, 30(5), 247-252 (1981)—Abstract only.
Kiura et al., "Bactericidal activity of electrolyzed acid water from solution containing sodium chloride at low concentration, in comparison with that at high concentration," *J Microbiol Methods*, 49(3), 285-93 (2002).
Koseki et al., "Decontamination of lettuce using acidic electrolyzed water," *J Food Prot.*, 64(5), 652-658 (2001).
Koseki et al., "Decontaminative effect of frozen acidic electrolyzed water on lettuce," *J Food Prot.*, 65(2), 411-414 (2002).
Koseki et al., "Effect of mild heat pre-treatment with alkaline electrolyzed water on the efficacy of acidic electrolyzed water against *Escherichia coli* O157:H7 and *Salmonella* on lettuce," *Food Microbiology*, 21(5), 559-566 (2004).
Koseki et al., "Effect of nitrogen gas packaging on the quality and microbial growth of fresh-cut vegetables under low temperatures," *J Food Prot.*, 65(2), 326-332 (2002).
Koseki et al., "Prediction of microbial growth in fresh-cut vegetables treated with acidic electrolyzed water during storage under various temperature conditions," *J Food Prot.*, 64(12), 1935-1942 (2001).
Kubota et al., "Effectiveness of acidic oxidative potential water in peritoneal lavage for perforated appendicitis," *Asian Journal of Surgery*, Department of Surgery, University of Hong Kong, Hong Kong., 22(3), pp. 282-284 (Jul. 1999).
Laing, P., "Diabetic Foot Ulcers," *Am J Surg*, 167, 31S-36S (1994).
Len et al., "Effects of storage conditions and pH on chlorine loss in electrolyzed oxidizing (EO) water," *J Agric Food Chem*, 50, 209-212 (2002).
Len et al., "Ultraviolet spectrophotometric characterization and bactericidal properties of electrolyzed oxidizing water as influenced by amperage and pH," *J Food Prot*, 63, 1534-1537 (2000).
Li et al., "Preliminary study of microbiocide effect and its mechanism of electrolyzed oxidizing water," *Chinese Journal of Epidemiology*, 17(2), 95-98 (1996).
Loshon et al., "Analysis of the killing of spores of Bacillus subtilis by a new disinfectant, Sterilox," *Journal of Applied Microbiology*, 91, 1051-1058 (2001).
Madden et al., "Application of Principles of Fluid Dynamics to Surgical Wound Irrigation," *Current Topics in Surgical Research*, 3: 85-93 (1971).
Mak et al., "Reactive Oxidant Species in Asthma," *Curr Opin Pulm Med*, vol. 12, pp. 7-11 (2006).
Mangram et al., "Guideline for *prevention of surgical site infection,*" *Infection* Control and Hospital Epidemiology, 20 (4): 247-278 (1999).
Marnett, L.J., "Oxyradicals and DNA damage," Carcinogenesis, 21(3), 361-370 (2000).
Martinez, F., "Sterilant for Human Wounds is Changing Patients' Lives" Infection Control Today, 3 pgs. (Nov. 2004), downloaded from http://www.infectioncontroltoday.com/articles/2004/11/sterilant-for-human-wounds-is-changing-patients-I.aspx.
MedlinePlus: AIDS [online] retrieved from http://www.nlm.nih.gov/medlineplus/ency/article/000594.htm on Jan. 16, 2010. May 30, 2009, pp. 1-6.
MedlinePlus: Asthma [online] retrieved from http://www.nlm.nih.gov/medlineplus/ency/article/000141.htm on Jan. 16, 2010. May 21, 2009, pp. 1-5.
MedlinePlus: Multiple Sclerosis [online] retrieved from http://www.nlm.nih.gov/medlineplus/ency/article/000737.htm on Jun. 11, 2009. Jan. 21, 2009, pp. 1-5.
MedlinePlus: Myocarditis [online] retrieved from http://www.nlm.nih.gov/medlineplus/ency/article/000149.htm on Jan. 16, 2010. May 15, 2008, pp. 1-4.
Michida et al., "Biomimetic oxidation of diphenyl sulfide with electrochemical P-450 model system in CH2Cl2 treated with alkaline solution," Yakugaku Zasshi—*Journal of the Pharmaceutical Society of Japan*, 119(10), 780-785 (1999).
Middleton et al., "Comparison of a solution of super-oxidized water (Sterilox) with glutaraldehyde for the disinfection of bronchoscopes, contaminated in vitro with Mycobacterium tuberculosis and Mycobacterium avium-intracellulare in sputum," Journal of Hospital Infection, 45, 278-282 (2000).
Miranda-Altamirano et al., "Treatment of 2nd and 3rd Degree Burns in 48 Pediatric Patients Without Routine Antibiotics Routine Using New Super-oxidized Water Technology" Abstract for Meeting of the Texas Surgical Society, San Antonio, TX, Apr. 1-3, 2005 (2 pgs).
Miyamoto et al., "Effectiveness of acidic oxidative potential water in preventing bacterial infection in islet transplantation," *Cell Transplantation*, 8, 405-411 (1999).
Model, et al., "Effectiveness of electrolyzed oxidized water irrigation in a burn-wound infection," *J Trauma Injury, Infection, and Critical Care*, 49, 511-514 (2000).
Morita et al., "Disinfection potential of electrolyzed solution containing sodium chloride at low concentrations," *J Virol Methods*, 85, 163-174 (2000).
Morris et al., "Biofilm: Why the Sudden Interest," *Journal of Otolaryngology*, vol. 34, Suppl. 2, pp. S56-S59 (2005).
Moscati et al., "Comparison of Normal Saline with Tap Water for Wound Irrigation," *American Journal of Emergency Medicine*, 16(4), 379-385 (1998).
Moyer et al., "Modulation of human fibroblast Gap junction intercellular communication by Hyaluronan," *J. Cell. Biol.* 196, 165-170 (2003).
Naderi et al., "Oxidative stress-induced apoptosis in dividing fibroblast involves activation of p38 MAP kinase and over expression of Bax: Resistance of quiescent cells to oxidative stress," *Apoptosis*, 8(1), 91-100 (2003).
Nagamatsu et al., "Application of electrolyzed acid water to sterilization of denture base part 1. Examination of sterilization effects on resin plate," Dent. Mater J, 20(2), 148-55, (2001)—Abstract only.
Nagamatsu et al., "Durability of bactericidal activity in electrolyzed neutral water by storage," *Dental Materials Journal*, 21(2), 93-104 (2002).
Nakae et al., "Effectiveness of electrolyzed oxidized water irrigation in a burn-wound infection model," J Trauma, 49(3): 511-514 (2000).
Nakae et al., "Electronlyzed Strong Acidid Water in a Burn Injury Model, on Usefulness of Hydrocolloid Dressing for Wound Healing," *Japanese Journal of Burn Injuries*, vol. 26, No. 2, p. 7 (2000).
Nakagawa et al., "Effect of rinsing hydrocolloid impressions using acidic electrolyzed water on surface roughness and surface hardness of stone models," J Oral Sci., 44(3-4), 141-146 (2002)—Abstract only.
Nakagawara et al., "Spectroscopic characterization and the pH dependence of bactericidal activity of the aqueous chlorine solution," Analytical Sciences, 14(4), 691-698 (1998).
Nelson, D., "Newer technologies for endoscope disinfection: electrolyzed acid water and disposable-component endoscope systems," Gasatrointestinal Endoscopy Clinics of North America, (Kerry Holland, Ed.) WB Saunders Co., Philadelphia, PA, vol. 10, No. 2, pp. 319-328 (2000).
Nomasa et al., "Sterilization of Dental Instruments by Electrolyzed Water and Their Corrosion Behaviors," *Journal of Kyushu Dental Society*, vol. 51, No. 6, pp. 784-799 (1997).
Ogino et al., "Treatment for abdominal aortic graft infection: irrigation with electrolyzed strong aqueous acid, in-situ grafting, and omentoplasty," Thorac Cardiovasc Surg, 48(1), 43-44 (2000).

(56) References Cited

OTHER PUBLICATIONS

Ohno et al., "Mediastinal Irrigation with Superoxidized Water After Open-Heart Surgery: The Safety and Pitfalls of Cardiovascular Surgical Application," Surgery Today, 30, 1055-1056 (2000).
Okubo et al., "Cytotoxicity and microbicidal activity of electrolyzed strong acid water and acidic hypochlorite solution under isotonic conditions," Kansenshogaku Zasshi: Journal of the Japanese Association for Infectious Diseases, 73(10), 1025-1031 (1999)—Abstract only.
O'Neill, "Physiological significance of volume-regulatory transporters," Am. J. Physiol., 276, C995-C1001 (1999).
Oomori et al., "The efficiency of disinfection of acidic electrolyzed water in the presence of organic materials," Analytical Science, 16, 365-369 (2000).
Otteneder et al., "Correlation of DNA adduct levels with tumor incidence: carcinogenic potency of DNA adducts," Mutat. Res., 424, 237-247 (1999).
Park et al., "Antimicrobial effect of electrolyzed water for inactivating Campylobacter jejuni during poultry washing," International Journal of Food Microbiology, 72(1-2), 77-83 (2002).
Park et al., "Effectiveness of electrolyzed water as a sanitizer for treating different surfaces," J Food Prot., 65(8), 1276-1280 (2002).
Park et al., "Effects of chlorine and pH on efficacy of electrolyzed water for inactivating *Escherichia coli* O157:H7 and *Listeria monocytogenes*," International Journal of Food Microbiology, 91(1), 13-18 (2004).
Perezous et al., "Colonization of *Candida*species in denture wearers with emphasis on HIV infection: A literature review," *Journal of Prosthetic Dentistry*, vol. 93, No. 3, pp. 288-293 (2005).
Piaggesi et al., "Sodium carboxyl-methyl-cellulose dressings in the management of deep ulcerations of diabetic foot," Diabet Med., 18(4), 320-324 (2001).
Plontke et al., "Transtympanic Endoscopy for Drug Delivery to the Inner Ear Using a New Microendoscope," *Adv. Otorhinolaryngol.*, vol. 59, pp. 149-155 (2002).
Powis et al., "Redox signaling and the control of cell growth and death," Pharmacol Ther., 68(1), 149-173 (1995).
Prutz, "Reactions of hypochlorous acid with biological substrates are activated catalytically by tertiary amines," *Archives of Biochemistry and Biophysics*, vol. 357, No. 2, pp. 265-273 (1998).
Rodeheaver et al., "Identification of the Wound Infection-Potentiating Factors in Soil," American Journal of Surgery, 128(1), 8-14, (1974).
Ruddy et al., "Decontamination in Practice: Endoscopic decontamination: an audit and practical review," Journal of Hospital Infection, 50, 261-268 (2002).
Russell, S.M., "The effect of electrolyzed oxidative water applied using electrostatic spraying on pathogenic and indicator bacteria on the surface of eggs," Poult. Sci., 82(1), 158-162 (2003).
Rutala et al., "New Disinfection and Sterilization Methods," Emerging Infectious Diseases, 7(2), 348-353 (2001).
Sakai, S., "Development of ionic electrolyzed water and its utilities. The preparation of ionic electrolyzed water and its application to disinfection," Kurin Tekunoroji, 6 (3): 53-57 (1996)—Abstract only.
Sakashita et al., "Antimicrobial effects and efficacy on habitually hand-washing of strong acidic electrolyzed water-a comparative study of alcoholic antiseptics and soap and tap water", Kansenshogaku Zasshi: The Journal of the Japanese Association on Infectious Diseases, 76, 373-377 (2002).
Sanders, L., "Diabetes Mellitus: Prevention of Amputation," J Am Pod Med Assoc, 84(7), 322-328 (1994).
Sawada et al., "Complete electrolysis using a microflow cell with an oil/water interface," Anal Chem., 74(5), 1177-1181 (2002).
Schaap et al., "Singlet Molecule Oxygen and Superoxide Dismutase," JACS, vol. 96, No. 12, pp. 4025-4026 (1974).
Sekiya et al., "The Use of Function Water for Treating Infected Skin Ulcers: Clinical Results," *Japanese Journal of Plastic Surgery*, vol. 38, No. 10, pp. 1051-1057 (1995).
Sekiya et al., "Treatment of Infectious Skin Defects or Ulcers with Electrolyzed Strong Acid Aqueous Solution," Artificial Organs, 21 (1), 32-38 (1997).
Selkon et al., "Evaluation of the antimicrobial activity of a new super-oxidized water, Sterilox®, for the disinfection of endoscopes," Journal of Hospital Infection, 41, 59-70 (1999).
Severino et al., "Is ?-galactosidase staining a marker of senescence in vitro and in vivo?" Exp. Cell. Res., 257(1), 162-171 (2000).
Sharma et al., "Treatment of *Escherichia coli* O157:H7 inoculated alfalfa seeds and sprouts with electrolyzed oxidizing water," International Journal of Food Microbiology, 86(3), 231-237 (2003).
Shen et al., "Interactions of selenium compounds with other antioxidants in DNA damage and apoptosis in Human normal keratinocytes," Cancer Epidemiology, Biomarkers, & Prevention, 10(4), 385-390 (2001).
Shetty et al., "Evaluation of microbicidal activity of a new disinfectant: Sterilox® 2500 against Clostridium difficile spores, Helicobacter pylori, cancomycin resistant *Enterococcus* species, *Candida albicans* and several *Mycobacterium* species," Journal of Hospital Infection, 41, 101-105 (1999).
Shimada et al., "A comparison of the bactericidal effects and cytotoxic activity of three types of oxidizing water, prepared by electrolysis, as chemical dental plaque control agents," *International Journal of Antimicrobial Agents*, vol. 15, No. 1, pp. 4-53 (2000).
Shimmura et al., "Acidic Electrolyzed Water in the Disinfection of the Ocular Surface," Experimental Eye Research, 70(1), 1-6 (2000).
Shirahata et al., "Electrolyzed-reduced water scavenges active oxygen species and protects DNA from oxidative damage," Biochem. Biophys. Res. Commun., 234(1), 269-274 (1997).
Singer et al., "Evaluation and Management of Traumatic Lacerations," New England Journal of Medicine, vol. 337., No. 16, pp. 1142-1148 (1997).
Smirnov et al., "Electron exchangers and electron- and ion-exchangers and their use in a water treatment system," Khim. Aktiv. Polim. Ikh Primen, 259-262 (1969)—Abstract only.
Solovyeva et al., "Cleaning effectiveness of root canal irrigation with electrochemically activated anolyte and catholyte solutions: a pilot study," International Endodontic Journal, 33, 494-504 (2000).
Soto et al., "Bacterial sulfate production by biodesulfurization of aromatic hydrocarbons, determined by ion chromatography," J Chromatogr A, 824(1), 45-52 (1998).
Soucek et al., "Clinical and histopathological aspects of ear disease in the acquired immunodeficiency syndrome," *Progress in Human Auditory and Vestibular Histopathology*, Kugler Publications, pp. 117-123 (1997).
Stein, G., "SV-40-transformed human fibroblasts: evidence for cellular aging in pre-crises cells," J Cell Physiol, 125, 36-44 (1985).
Stevenson et al., "Cleansing the Traumatic Wound by High Pressure Syringe Irrigation," JACEP, 5(1), 17-21 (1976).
Subrahmanyam, "Topical Application of Honey in Treatment of Burns," *British Journal of Surgery*, vol. 78, pp. 497-498 (1991).
Sumita et al., "Characteristics and use of acidified water from redox water generator," Shokuhin Kogyo, 40(10), 29-36 (1997)—Abstract only.
Suzuki et al., "Novel products generated from 2'-deoxyguanosine by hypochlorous acid or a myeloperoxidase -H2O2-Cl-system: identification of diimino-imidazole and amino-imidazolone nucleosides," Nucleic Acids Res., 30(11), 2555-2564 (2002).
Takeshita et al., "Influence of free residual chlorine concentration and pH on bactericidal effects of electrolyzed water," Bokin Bobai, 29(2), 69-72 (2001).
Takeyoshi et al., "Primary eye irritation and 5-day cumulative skin irritation studies of super oxidized water in rabbits," Oyo Yakuri, 48(3), 173-177 (1994)—Abstract only.
Tanaka et al., "Antimicrobial activity of superoxidized water" Journal of Hospital Infection, 34, 43-49 (1996).
Tanaka et al., "Molecular basis of antiapoptotic effect of immunophilin ligands on hydrogen peroxide-induced apoptosis in human glioma cells," Neurochem Res., 29(8), 1529-1536 (2004).
Tanaka et al., "The use of electrolyzed solutions for the cleaning and disinfecting of dialyzers" Artif. Organs, 24(12), 921-928 (2000).

(56) References Cited

OTHER PUBLICATIONS

Tateno et al., "MT-4 plaque formation can distinguish cytopathic substypes of the human immunodeficiency virus (HIV)," Virology, 167, 299-301 (1988).
Thurnheer et al., "Mass Transport of Macromolecules within an In Vitro Model of Supragingival Plaque," *Applied and Environmental Microbiology*, vol. 69, No. 3, pp. 1702-1709 (2003).
Upright et al., "Evaluation of Mesalt dressings and continuous wet saline dressings in ulcerating metastatic skin lesions," Cancer Nursing, 17(2), 149-155 (1994).
Valko et al., "Role of oxygen radicals in DNA damage and cancer incidence," Mol Cell Biochem, 266, 37-56 (2004).
Van Britsom et al., "A rapid method for the detection of uranium in surface water," Sci. Total Environ., vols. 173/174, pp. 83-89 (1995).
Venkitanarayanan et al., "Efficacy of Electrolyzed Oxidizing Water for Inactivating *Escherichia coli* O157:H7, *Salmonella enteritidis*, and *Listeria* monocytogenes," Applied and Environmental Microbiology, 65 (9), 4276-4279 (1999).
Veves et al., "A randomized, controlled trial of Promogran (a collagen/oxidized regenerated cellulose dressing) vs standard treatment in the management of diabetic foot ulcers," Arch Surg., 137(7), 822-827 (2002).
Winter, "Formation of the Scab and the Rate of Epithelization of Superficial Wounds in the Skin of the Young Domestic Pig," Nature, 193, 293-294 (1962).
Xakellis et al., "Hydrocolloid versus saline-gauze dressings in treating pressure ulcers: a cost-effectiveness analysis," Arch Phys Med Rehabil., 73(5), 463-9 (1992).
Yahagi et al., "Effect of Electrolyzed Water on Wound Healing," Artificial Organs, 24(12), 984-987 (2000).
Yang et al., "The effect of pH on inactivation of pathogenic bacteria on fresh-cut lettuce by dipping treatment with electrolyzed water," Journal of Food Science, 68(3), 1013-1017 (2003).
Yoshimoto et al., "Virucidal effect of super oxidized water" Kagaku Ryoho no Ryoiki, 12(7), 1337-1342 (1996)—Abstract only.
Young et al., "Mechanisms of killing of Bacillus subtilis spores by hypochlorite and chlorine dioxide," J Appl Microbiol, 95, 54-67 (2003).
Zhang et al., "Antioxidant superoxide dismutase attenuates increased endothelial permeability induced by platelet activating factor," Soc Gynecol Investig. 10, 5-10 (2003).
Zinkevich et al., "The effect of super-oxidized water on *Escherichia coli*," Journal of Hospital Infection, 46, 153-156 (2000).
European Patent Office, Partial International Search Report and Invitation to Pay Additional Search Fees for International Application No. PCT/US2004/043961 (dated Oct. 4, 2005).
European Patent Office, Supplementary European Search Report for European Patent Application No. 02790029 (dated Aug. 24, 2005).
European Patent Office, European Search Report for European Patent Application No. 1 103 264 (dated Sep. 24, 2003).
European Patent Office, European Search Report for European Patent Application No. 1 293 481 (dated Nov. 6, 2003).
European Patent Office, International Search Report for International Application No. PCT/US2007/060860 (dated Sep. 4, 2007).
U.S. Patent & Trademark Office, International Search Report for International Application No. PCT/US02/38861 (dated Feb. 24, 2003).
U.S. Patent & Trademark Office, Office Action in U.S. Appl. No. 10/146,140 (dated Mar. 3, 2006).
European Patent Office, International Search Report for International Application No. PCT/US2006/011251 (dated Sep. 14, 2006).
European Patent Office, Written Opinion of the International Searching Authority for International Application No. PCT/US2006/011251 (dated Sep. 14, 2006).
European Patent Office, International Search Report for International Application No. PCT/US2006/011252 (dated Nov. 10, 2006).
European Patent Office, Written Opinion of the International Searching Authority for International Application No. PCT/US2006/011252 (dated Nov. 10, 2006).
Annex to Form PCT/ISA/206, Communication Relating to the Results of the Partial International Search for PCT/US2006/016856 (dated Dec. 27, 2006).
European Patent Office, International Search Report for International Application No. PCT/US2006/016856 (dated Feb. 2, 2007).
European Patent Office, International Search Report for International Application No. PCT/US2007/060854 (dated Sep. 4, 2007).
European Patent Office, International Search Report for International Application No. PCT/US2007/060856 (dated Aug. 31, 2007).
European Patent Office, Written Opinion of the International Searching Authority for International Application No. PCT/US2007/060854 (dated Sep. 4, 2007).
European Patent Office, Written Opinion of the International Searching Authority for International Application No. PCT/US2007/060856 (dated Aug. 31, 2007).
European Patent Office, Written Opinion of the International Searching Authority for International Application No. PCT/US2007/060860 (dated Sep. 4, 2007).
International Preliminary Report on Patentability for PCT/US2006/016856, dated Nov. 6, 2007.
European Patent Office, European Search Report for European Patent Application No. 00124968.9 (dated Sep. 24, 2003).
European Patent Office, European Search Report for European Patent Application No. 02020429 (dated Oct. 30, 2003).
International Search Report in PCT/US2004/043961 (dated Nov. 25, 2005).
European Patent Office, International Search Report in International Application PCT/US2009/069345 (dated Jun. 25, 2010).
European Patent Office, International Search Report in International Application No. PCT/US2008/056919 (dated Jun. 26, 2008).
European Patent Office, International Preliminary Report on Patentability in International Application No. PCT/US2008/056919 (dated Sep. 15, 2009).
U.S. Patent and Trademark Office, International Search Report and Written Opinion in International Application No. PCT/US2010/038697 (dated Dec. 29, 2011).
U.S. Patent and Trademark Office, International Search Report and Written Opinion in International Application No. PCT/US2010/034238 (dated Jul. 1, 2010).
U.S. Patent and Trademark Office, International Preliminary Report on Patentability in International Application No. PCT/US2010/034238 (dated Nov. 24, 2011).
European Patent Office, European Search Report for European Patent Application No. 10775333.7 (dated Dec. 18, 2013).
European Patent Office, European Search Report for European Patent Application No. 10805132.7 (dated Feb. 6, 2014).
Wang et al., "Hypochlorous Acid as a Potential Wound Care Agent," *Journal of Burns and Wounds*, vol. 6, pp. 65-79 (2007).
Korean Intellectual Property Office, Notification of Preliminary Rejection for Korean Patent Application No. 10-2012-7000196 (dated Jul. 26, 2016).

\* cited by examiner
† cited by third party

SOLUTION CONTAINING HYPOCHLOROUS ACID AND METHODS OF USING SAME

CROSS-REFERENCE TO RELATED APPLICATIONS

This application is a national stage entry of International Patent Application No. PCT/US2010/038697 under 35 U.S.C. § 371, filed Jun. 15, 2010, which claims priority to U.S. Provisional Application No. 61/268,764, filed Jun. 15, 2009, each of which is incorporated herein in its entirety.

FIELD OF THE INVENTION

This invention pertains to low pH antimicrobial solutions and methods of using such solutions.

BACKGROUND OF THE INVENTION

Free Available Chlorine (FAC) water solutions, also known as super-oxidized water solutions, have shown wide use as disinfectants and wound treatment therapies because of their rapid and highly antimicrobial activity against a wide range of bacteria, viruses, and spores. FAC water solutions are typically environmentally safe and, thus, avoid the need for costly disposal procedures. Additionally, FAC water solutions do not promote microbial resistance or tolerance which can be developed with conventional antibiotic therapy. These solutions typically have a pH between 5 and 7 and contain an elevated concentration of a number of highly reactive chlorine species (e.g., hypochlorous acid, sodium hypochlorite, etc.) and other oxidative species which provide antimicrobial properties.

Although standard FAC water solutions are effective disinfectants, they generally have an extremely limited shelf-life (usually only a few hours) due to the reactivity of the chlorine and oxidative species present therein. As a result of this short lifespan, the production of FAC water must often take place in close proximity to where the FAC water is to be used as a disinfectant. This means that a healthcare facility, such as a hospital, must purchase, house and maintain the equipment necessary to produce FAC water. In addition, given their highly reactive and nonselective nature, standard FAC water solutions can often be inactivated by organic load present in a wound site, thereby limiting their effectiveness as wound treatment therapies.

Accordingly, there remains a need for new disinfectants and wound treatment therapies that address the shortcomings of the standard FAC water solutions discussed above. The invention provides such methods. These and other advantages of the invention, as well as additional inventive features, will be apparent from the description of the invention provided herein.

BRIEF SUMMARY OF THE INVENTION

The present invention relates to low pH antimicrobial solutions comprising hypochlorous acid and water. The inventive low pH antimicrobial solutions have a pH from about 4 to about 6 and may further comprise a buffer. Such solutions can be used to treat impaired or damaged tissue and to disinfect the surface of biological and/or inanimate objects.

The invention further provides processes for the production of low pH antimicrobial solutions comprising hypochlorous acid and water. One inventive process comprises a chemical procedure wherein chlorine gas is added to a buffer solution containing a buffering agent and water. In another embodiment, the low pH antimicrobial solutions can be produced using an electrochemical process. In certain aspects of the invention, both the chemical and electrochemical processes can be continuous.

BRIEF DESCRIPTION OF THE DRAWINGS

The present invention will be described with reference to the attached drawing by way of a non-limiting example only, in which.

DETAILED DESCRIPTION OF THE INVENTION

The present invention relates to low pH antimicrobial solutions comprising hypochlorous acid and water. The low pH antimicrobial solutions of the invention may be any acidic pH of from about 1 to about 7. In this regard, the antimicrobial solutions can be any low pH such that they can be safely applied in suitable quantities to surfaces without damaging the surfaces or harming objects, such as human skin, that comes into contact with the solutions. Typically, the pH of the antimicrobial solution is from about 4 to about 6. In a further embodiment, the antimicrobial solutions of the present invention have a pH from about 4.9 to about 5.6. The antimicrobial solutions have a pH from about 4.5 to about 5.6 in another embodiment.

The water employed in the low pH antimicrobial solutions can be any suitable water. For example, the water can be any medically or pharmaceutically acceptable water including purified water and USP grade water. Preferably, the purified water is deionized water or reverse osmosis water. Other exemplary sources of water can be municipally supplied commercial, residential, or industrial water. In a preferred embodiment, the water is purified water which is purified by a process such as reverse osmosis, deionization, or distillation.

Various ionic and other species may be present in the low pH antimicrobial solutions of the present invention. For example, the antimicrobial solutions may contain chlorine. Preferably, the chlorine species present is free chlorine. The presence of one or more chlorine species is believed to contribute to the antimicrobial and disinfectant ability of the solutions.

Free chlorine typically includes, but is not limited to, hypochlorous acid (HClO), hypochlorite ions (ClO$^-$), dissolved chlorine gas (Cl$_2$), and other radical chlorine species.

Hypochlorous acid and hypochlorite exist in a pH-dependent equilibrium. Thus, while in no way limiting the present invention, it is believed that the control of pH as set forth above permits a stable antimicrobial solution in which hypochlorite (e.g., sodium hypochlorite) and chloride ions are present in low quantities and hypochlorous acid content is maximized. This is in contrast to commonly known chlorine-containing solutions which owe their biocidal activity to high relative concentrations of hypochlorite and chloride (which leads to the formation of more rapidly reactive chlorine species), not hypochlorous acid.

In this regard, the low pH antimicrobial solutions of the present invention comprise hypochlorous acid in any suitable amount required to achieve the desired antimicrobial activity. Typically, the solutions comprise hypochlorous acid in an amount from about 5 mg/L to about 200 mg/L. In another embodiment of the present invention, the solutions comprise hypochlorous acid in an amount from about 7 mg/L to about 110 mg/L.

Free available chlorine (FAC) species (i.e., diatomic chlorine, hypochlorous acid, and hypochlorite) may be present in the low pH antimicrobial solutions of the present invention in any suitable amount such that the desired antimicrobial activity is achieved. Typically, the inventive solutions have a FAC content from about 10 mg/L to about 250 mg/L. In another embodiment of the present invention, free available chlorine is present in an amount from about 60 mg/L to about 150 mg/L.

As discussed above, the low pH antimicrobial solutions of the present invention comprise chloride ions in a low amount relative to previously known chlorine-containing antimicrobial solutions. The chloride ion content can be any suitable amount such that the hypochlorous acid levels in the inventive solutions can be maintained in the amount required to provide the desired antimicrobial activity. Exemplary low pH antimicrobial solutions contain chloride ions in an amount from about 4 mg/L to about 120 mg/L. In another embodiment of the present invention, chloride ions are present in an amount from about 4 mg/L to about 75 mg/L. More preferably, chloride ions are present in the solutions of the present invention in an amount from about 4 mg/L to about 65 mg/L.

The levels of the various ionic and other species present in the low pH antimicrobial solutions of the present invention may be measured by any suitable methods known in the art. For example, chlorine content may be measured by methods, such as the DPD colorimeter method (Lamotte Company, Chestertown, Md.) or other known methods established by the Environmental Protection Agency. In the DPD colorimeter method, a yellow color is formed by the reaction of free chlorine with N,N-diethyl-p-phenylenediamine (DPD) and the intensity is measured with a calibrated calorimeter that provides the output in parts per million. Further addition of potassium iodide turns the solution a pink color to provide the total chlorine value. Another known method for measuring free chlorine is to measure the absorption of ultraviolet (UV) light at specific wavelengths. This method allows for measurement of hypochlorous acid and hypochlorite individually as each species has a unique absorption spectrum.

In one embodiment of the present invention, the low pH antimicrobial solutions of the present invention can further comprise a buffering agent. The buffering agent can be present in any suitable amount so as to maintain the pH at the desired levels set forth above. Similarly, any suitable buffering agent or combination of buffering agents may be used in connection with the inventive composition. Examples of suitable buffering agents include citrate, acetate, succinate, borate, formate, benzoate, carbonate, propionate, phosphate, salts thereof, and combinations thereof. In one embodiment, the low pH antimicrobial solutions of the present invention contain a phosphate buffer. In a preferred embodiment, the buffering agent is a phosphate selected from the group consisting of sodium phosphate monobasic, sodium phosphate dibasic, and combinations thereof. More preferably, the buffering agent is a combination of sodium phosphate monobasic and sodium phosphate dibasic.

The present invention additionally provides a method of treating impaired or damaged tissue, which method comprises contacting the impaired or damaged tissue with a therapeutically effective amount of the low pH antimicrobial solution of the present invention.

As used herein, a "therapeutically effective amount" of the solution administered to the tissue of a patient (e.g., an animal, particularly a human) in the context of the present invention should be sufficient to affect a therapeutic or prophylactic response in the tissue over a reasonable time frame. The dose can be readily determined using methods that are well known in the art. One skilled in the art will recognize that the specific dosage level for any particular tissue will depend upon a variety of factors. For example, the dose can be determined based on the strength of the particular low pH antimicrobial solution employed, the severity of the condition, the body weight of the patient, the age of the patient, the physical and mental condition of the patient, general health, sex, diet, and the like. The size of the dose also can be determined based on the existence, nature, and extent of any adverse side effects that might accompany the administration of a particular low pH antimicrobial solution. It is desirable, whenever possible, to keep adverse side effects to a minimum.

Factors which can be taken into account for a specific dosage can include, for example, bioavailability, metabolic profile, time of administration, route of administration, rate of excretion, pharmacodynamics associated with a particular low pH antimicrobial solution in a particular patient, and the like. Other factors can include, for example, the potency or effectiveness of the solution with respect to the particular impairment or damage to be treated, the severity of the symptoms presented prior to or during the course of treatment, and the like. In some instances, what constitutes a therapeutically effective amount also can be determined, in part, by the use of one or more of the assays, e.g., bioassays, which are reasonably clinically predictive of the efficacy of a particular low pH antimicrobial solution for the treatment of impaired or damaged tissue.

One of ordinary skill in the art will recognize that the low pH antimicrobial solution of the present invention can be used to contact impaired or damaged tissue either alone or in combination with one or more other therapeutic agents. In one embodiment the one or more other therapeutic agents are administered for the same purpose as the low pH antimicrobial solution (i.e., to treat impaired or damaged tissue). In yet another embodiment, the one or more other therapeutic agents are administered to treat or prevent a related condition such as, for example, inflammatory conditions or allergic reactions.

Similarly, the low pH antimicrobial solution of the present invention can be administered in combination with one or more pharmaceutically acceptable carriers, vehicles, adjuvants, excipients, or diluents, which are known in the art. One skilled in the art can determine the appropriate formulation and method of administration for administering the solution in accordance with the present invention.

Any suitable method can be used for contacting the impaired or damaged tissue, so as to treat the impaired or damaged tissue in accordance with the present invention. For example, the impaired or damaged tissue can be treated in accordance with the invention by irrigating the tissue with the low pH antimicrobial solution of the invention, so as to contact the impaired or damaged tissue with the solution.

Alternatively (and additionally), the low pH antimicrobial solution of the present invention can be administered as a steam or a spray, or by aerosolization, nebulization or atomization, as described herein, so as to contact the impaired or damaged tissue with the solution.

When the low pH antimicrobial solution of the invention is administered by aerosolization, nebulization or atomization, it is preferably administered in the form of droplets having a diameter in the range of from about 1 micron to about 10 microns. Methods and devices, which are useful for aerosolization, nebulization and atomization, are well known in the art. Medical nebulizers, for example, have been used to deliver a metered dose of a physiologically active liquid into an inspiration gas stream for inhalation by a recipient. See, e.g., U.S. Pat. No. 6,598,602. Medical nebulizers can operate to generate liquid droplets, which form an aerosol with the inspiration gas. In other circumstances medical nebulizers may be used to inject water droplets into an inspiration gas stream to provide gas with a suitable moisture content to a recipient, which is particularly useful where the inspiration gas stream is provided by a mechanical breathing aid such as a respirator, ventilator or anaesthetic delivery system.

An exemplary nebulizer is described, for example, in WO 95/01137, which describes a hand held device that operates to eject droplets of a medical liquid into a passing air stream (inspiration gas stream), which is generated by a recipient's inhalation through a mouthpiece. Another example can be found in U.S. Pat. No. 5,388,571, which describes a positive-pressure ventilator system which provides control and augmentation of breathing for a patient with respiratory insufficiency and which includes a nebulizer for delivering particles of liquid medication into the airways and alveoli of the lungs of a patient. U.S. Pat. No. 5,312,281 describes an ultrasonic wave nebulizer, which atomizes water or liquid at low temperature and reportedly can adjust the size of mist. In addition, U.S. Pat. No. 5,287,847 describes a pneumatic nebulizing apparatus with scalable flow rates and output volumes for delivering a medicinal aerosol to neonates, children and adults. Further, U.S. Pat. No. 5,063,922 describes an ultrasonic atomizer.

The method of the present invention can be used in the treatment of tissues, which have been impaired or damaged, for example, by surgery. In one embodiment, the method of the present invention can be used for treating tissues which have been impaired or damaged by an incision. In additional embodiments, the method of the present invention can be used for treating tissues, which have been impaired or damaged by oral surgery, graft surgery, implant surgery, transplant surgery, cauterization, amputation, radiation, chemotherapy, and combinations thereof. The oral surgery can include, for example, dental surgery such as, for example, root canal surgery, tooth extraction, gum surgery, and the like.

The method of the present invention also includes treating tissues, which have been impaired or damaged by non-surgical means. For example, the low pH antimicrobial solution of the present invention can be used to treat one or more burns, cuts, abrasions, scrapes, rashes, ulcers, puncture wounds, combinations thereof, and the like, which are not necessarily caused by surgery. The method of the present invention also can be used for treating impaired or damaged tissue, which is infected, or tissue impaired or damaged due to infection. Such infection can be caused by one or more infectious pathogens, such as, for example, one or more microorganisms selected from the group consisting of viruses, bacteria, fungi, and combinations thereof as described herein.

The viruses can include, for example, one or more viruses selected from the group consisting of adenoviruses, human immunodeficiency virus (HIV), rhinoviruses, flu viruses (e.g., influenza A), hepatitis (e.g., hepatitis A), coronavirus (responsible for Severe Acute Respiratory Syndrome (SARS)), rotavirus, respiratory syncytial virus, herpes simplex virus, varicella zoster virus, rubella virus, and other susceptible viruses. The bacteria can include, for example, one or more bacteria selected from the group consisting of *Escherichia coli, Pseudomonas aeruginosa, Staphylococcus aureus, Bacillus athrophaeus, Streptococcus pyogenes, Salmonella choleraesuis, Shingella dysenteriae, Mycobaterium tuberculosis*, and other susceptible bacteria. The fungi and yeasts that may be treated with the low pH antimicrobial solution of the present invention can include, for example, one or more of *Candida albicans, Bacillus subtilis, Trichophyton mentagrophytes*, and *Bacillus athrophaeus*.

In a further embodiment, the low pH antimicrobial solution of the present invention is effective against a wide range of gram positive and gram negative organisms, as set forth herein, even in the presence of moderate to high levels of organic load (e.g., the decomposing biological material at the site of a wound). Such activity is in contrast with previously known chlorine-containing solutions, wherein moderate to high levels of organic load are know to inhibit antimicrobial activity.

The present invention further provides a method of disinfecting a surface, which method comprises contacting the surface with an effective amount of the low pH antimicrobial solution of the present invention. In accordance with the method of the present invention, the surface can be contacted using any suitable method. For example, the surface can be contacted by irrigating the surface with the solution of the invention, so as to disinfect the surface in accordance with the invention. Additionally, the surface can be contacted by applying the low pH antimicrobial solution of the present invention to the surface as a steam or a spray, or by aerosolization, nebulization or atomization, as described herein, so as to disinfect the surface in accordance with the invention. Further, the solution of the present invention can be applied to the surface via a substrate such as, for example, a cleaning wipe, cloth, sponge, brush, etc.

By disinfecting a surface in accordance with the present invention, the surface may be cleansed of infectious microorganisms such as, for example, viruses, bacteria, fungi, and combinations thereof as described herein. Alternatively (or additionally), the low pH antimicrobial solution of the present invention can be applied to the surface to provide a barrier to infection, thereby disinfecting a surface in accordance with the present invention.

The method of the present invention can be used for disinfecting a surface, which is biological, inanimate, or a combination thereof. Biological surfaces can include, for example, tissues within one or more body cavities such as, for example, the oral cavity, the sinus cavity, the cranial cavity, the abdominal cavity, and the thoracic cavity. Tissues within the oral cavity include, for example, mouth tissue, gum tissue, tongue tissue, and throat tissue. The biological tissue also can include muscle tissue, bone tissue, organ tissue, mucosal tissue, and combinations thereof. In accordance with the method of the present invention, the surfaces of internal organs, viscera, muscle, and the like, which may be exposed during surgery, can be disinfected, for example, to maintain sterility of the surgical environment. Inanimate surfaces include, for example, surgically implantable devices, prosthetic devices, and medical devices. Additional examples of inanimate surfaces include any non-biological surface which may require disinfecting such as, for example, floors, counters, household-related hard surfaces, circuitry, hard drives, etc.

The low pH antimicrobial solution of the present invention is generally stable for at least twenty-hours, and typically at least two days. More typically, the solution is stable for at least one week (e.g., one week, two weeks, three weeks, four weeks, etc.), and preferably at least two months. More preferably, the solution is stable for at least six months after its preparation. Even more preferably, the solution is stable for at least one year, and most preferably for at least three years.

As used herein, the term stable generally refers to the ability of the low pH antimicrobial water solution to remain suitable for its intended use, for example, in decontamination, disinfection, sterilization, anti-microbial cleansing, and wound cleansing, for a specified period of time after its preparation under normal storage conditions (i.e., room temperature). In this regard, the low pH antimicrobial solution of the present invention is also stable when stored under accelerated conditions, typically about 30° C. to about 60° C., for at least 90 days, and preferably 180 days.

The concentrations of ionic and other species present in solution are generally maintained during the shelf-life of the low pH antimicrobial solution. Typically, the concentrations of free available chlorine species are maintained at about 70% or greater from their initial concentration for at least two months after preparation of the low pH antimicrobial solution. Preferably, these concentrations are maintained at about 80% or greater of their initial concentration for at least two months after preparation of the solution. More preferably, these concentrations are at about 90% or greater of their initial concentration for at least two months after preparation of the solution, and most preferably, about 95% or greater.

The stability of the low pH antimicrobial solution of the present invention may be determined based on the reduction in the amount of live microorganisms present in a sample following exposure to the solution. The measurement of the reduction of organism concentration may be carried out using any suitable organism including bacteria, fungi, yeasts, or viruses, as described herein. The low pH antimicrobial solution is useful as both a low-level disinfectant capable of a four log ($10^4$) reduction in the concentration of live microorganisms and a high-level disinfectant capable of a six log ($10^6$) reduction in concentration of live microorganisms.

In one embodiment of the present invention, the low pH antimicrobial solution is capable of yielding at least a four log ($10^4$) reduction in total organism concentration following exposure for one minute, when measured at least two months after preparation of the solution. Preferably, the solution is capable of such a reduction of organism concentration when measured at least six months after preparation of the solution. More preferably, the solution is capable of such a reduction of organism concentration when measured at least one year after preparation, and most preferably when measured at least three years after preparation.

In another embodiment the present invention, the low pH antimicrobial solution is capable of yielding at least a six log ($10^6$) reduction in total organism concentration within one minute of exposure, when measured at least two months after preparation of the solution. Preferably, the FAC water solution is capable of achieving this reduction when measured at least six months after preparation, and more preferably at least one year after preparation. Preferably, the FAC water solution is capable of at least a seven log ($10^7$) reduction in the concentration of live microorganisms within one minute of exposure, when measured at least two months after preparation.

The present invention further provides processes for producing the low pH antimicrobial solutions of the present invention. In one embodiment, the low pH antimicrobial solutions can be produced by an oxidation-reduction process (i.e., an electrolytic or redox reaction) in which electrical energy is used to produce chemical change in an aqueous solution. Electrical energy is introduced into and transported through water by the conduction of electrical charge from one point to another in the form of an electrical current. In order for the electrical current to arise and subsist there must be charge carriers in the water, and there must be a force that makes the carriers move. The charge carriers can be electrons, as in the case of metal and semiconductors, or they can be positive and negative ions in the case of solutions.

In the case of the present invention, the low pH antimicrobial solutions can be produced using at least one electrolysis cell comprising an anode chamber, cathode chamber, and salt solution chamber located between the anode and cathode chambers. A reduction reaction occurs at the cathode while an oxidation reaction occurs at the anode in the process for preparing a solution according to the invention. The specific reductive and oxidative reactions that occur are described in International Application WO 03/048421 A1. As used herein, water produced at an anode is referred to as anode water and water produced at a cathode is referred to as cathode water. Anode water contains oxidized species produced from the electrolytic reaction while cathode water contains reduced species from the reaction.

Anode water generally has a low pH typically of from about 1 to about 6.8. Anode water generally contains chlorine in various forms including, for example, chlorine gas, chloride ions, hydrochloric acid and/or hypochlorous acid. Oxygen in various forms is also present including, for example, oxygen gas, peroxides, and/or ozone. Cathode water generally has a high pH typically of from about 7.2 to about 11. Cathode water generally contains hydrogen gas, hydroxyl ions, and/or sodium ions.

The source of the water for the anode chamber and cathode chamber of the electrolysis cell may be any suitable water supply. The water may be from a municipal water supply or alternatively pretreated prior to use in the electrolysis cell. Preferably, the pretreated water is selected from the group consisting of softened water, purified water, distilled water, and deionized water. More preferably, the pretreated water source is ultrapure water obtained using reverse osmosis purification equipment.

The salt water solution for use in the salt water chamber may be any aqueous salt solution that contains suitable ionic species to produce the low pH antimicrobial solution. Preferably, the salt water solution is an aqueous sodium chloride (NaCl) salt solution, also commonly referred to as a saline solution. Other suitable salt solutions include other chloride salts such as potassium chloride, ammonium chloride and magnesium chloride as well as other halogen salts such as potassium and bromine salts. The salt solution may contain a mixture of salts.

The low pH antimicrobial solutions of the present invention comprise a mixture of anode water and cathode water produced in the electrochemical process described above. Accordingly, in a preferred embodiment, the electrochemical cell described above further comprises a mixing tank connected to and downstream of the anode chamber and the cathode chamber. Further, the mixing tank may optionally include suitable devices for monitoring the level and pH of the solution. In this manner, anode water, cathode water, and, optionally, a buffering agent, may be mixed together in any suitable ratio so as to provide for the desired pH as described above.

In another embodiment of the present invention, the low pH antimicrobial solutions of the present invention can be produced by chemical process wherein chlorine is added to a buffer solution comprising a buffering agent and water.

The source of the water for the chemical process may be any suitable water supply. The water may be from a municipal water supply or alternatively pretreated prior to use in the electrolysis cell. Preferably, the pretreated water is selected from the group consisting of softened water, purified water, distilled water, and deionized water. More preferably, the pretreated water source is ultrapure water obtained using reverse osmosis purification equipment.

The chlorine can be added to the buffer solution in any suitable form. For example, the chlorine can be added to the buffer solution as an aqueous solution or a gas. Preferably, the chlorine is added to the buffer solution as a gas. Similarly, the chlorine can be added by any suitable means. Exemplary means for adding chlorine to the buffer solution include, for example, continuous spraying and bubbling. Most preferably, chlorine gas is bubbled into the buffer solution. Chlorine can be added to the buffer solution in any suitable amount and rate such that the desired pH and component content (e.g., free available chlorine) are obtained.

Following its preparation, the low pH antimicrobial solution of the present invention may be transferred to a sealed container for distribution and sale to end users such as, for example, health care facilities including hospitals, nursing homes, doctor offices, outpatient surgical centers, dental offices, and the like. Any suitable sealed container may be used that maintains the sterility and stability of the low pH antimicrobial solution held by the container. The container may be constructed of any material that is compatible with the solution and should be generally non-reactive so that the ions present in the solution do not react with the container to any appreciable extent.

Preferably, the container is constructed of plastic or glass. The plastic may be rigid so that the container is capable of being stored on a shelf. Alternatively, plastic may be flexible, such as a flexible bag.

Suitable plastics include polypropylene, polyethylene terephthalate (PET), polyolefin, cycloolefin, polycarbonate, ABS resin, polyethylene, polyvinyl chloride, and mixtures thereof. Preferably, the container comprises polyethylene selected from the group consisting of high-density polyethylene (HDPE), low-density polyethylene (LDPE), and linear low-density polyethylene (LLDPE). Most preferably, the container is high density polyethylene or polyethylene terephthalate.

The container has an opening to permit dispensing of the low pH antimicrobial solution. The container opening may be sealed in any suitable manner. For example, the container may be sealed with a twist-off cap or stopper. Optionally, the opening may be further sealed with a foil layer.

The headspace gas of the sealed container may be air or other suitable gas that does not react with the low pH antimicrobial solution. Suitable headspace gases included nitrogen, oxygen, and mixtures thereof.

The following examples further illustrate the invention but, of course, should not be construed as in any way limiting its scope.

Example 1

This example demonstrates one embodiment of the present invention wherein 1 liter of low pH antimicrobial solution is produced by a chemical process comprising the addition of chlorine to a buffer solution.

1.0 g sodium phosphate monobasic ($NaH_2PO_4$) and 1.08 g sodium phosphate dibasic ($Na_2HPO_4.7H_2O$) is added to 1 liter of purified water (RO, DI, or distilled water) and stirred to provide a dilute buffer solution with a pH of approximately 8.0. Chlorine gas ($Cl_2$) is slowly bubbled into the dilute buffer solution until the free available chlorine content reaches a level of 150 mg/L. The resulting low pH antimicrobial solution has a pH of 5.6.

Example 2

This example demonstrates another embodiment of the present invention wherein an electrochemical process is employed to produce a low pH antimicrobial solution.

A dilute buffer solution is prepared by adding sodium phosphate monobasic ($NaH_2PO_4$) and sodium phosphate dibasic ($Na_2HPO_4$) to 10 liters of process water with stirring. Amounts of the phosphate salts to be added to the process water, depending on their hydration, are provided below:

Sodium phosphate monobasic (one of the following):
1. 1430 g $NaH_2PO_4$,
2. 1645 g $NaH_2PO_4.H_2O$, or
3. 1859 g $NaH_2PO_4.2H_2O$ Sodium phosphate dibasic (one of the following):
1. 64 g $Na_2HPO_4$
2. 121 g $Na_2HPO_4.7H_2O$
3. 161 g $Na_2HPO_4.12H_2O$ It should take between 5-10 minutes for the salts to dissolve. After the salts dissolve, the solution should be clear with no sign of particles and the pH of the solution should be approximately pH 4.7.

The buffer solution is added separately to cathode water and anode water supplied by a three chamber electrochemical cell. The buffer solution is added at a rate of 1% of the total cathode and anode flow (for both cells). For example, if the anode flow for each cell is 3 liters/minute and the cathode flows 2 liters/minute, the total flow for the system is 10 liters/minute and the phosphate buffer would be added at 100 ml/min. The phosphate solution is added using a peristaltic pump into anode water and cathode water mixing compartments prior to pH and ORP measurement. The addition line is split into two lines directly before the addition point so that buffer solution is added to each mixing compartment (i.e., anode water mixing compartment and cathode water mixing compartment). The anode water and cathode water are then mixed to provide a solution with a free available chlorine level of 140-150 ppm and a pH of 5.5-5.8.

The low pH antimicrobial solution is then packaged in 120 mL PET bottles which can be fitted with finger spray caps.

Example 3

This example demonstrates the stability of the low pH antimicrobial solution of the present invention. One lot of the low pH antimicrobial solution produced above in Example 2 (i.e., via the electrochemical process) was subjected to stability testing at 40° C. one (1) sample per lot; one (1) sample per time point. The solution was packaged in 120 mL PET containers with a finger pump spray head that was secured in the bottle at the time of production. Samples were placed in an Environmental Test Chamber set at 40° C.±2° C. for accelerated testing. Lot release data represented T=0. Each data point was represented by an unopened bottle.

A total of forty bottles, with finger spray caps, were tested at various time points in order to establish an accelerated shelf-life determination. One bottle was tested at each time point. Each bottle was tested for free available chlorine content and pH at designated time points. Samples were tested and analyzed to meet the following acceptance criteria:

| Test | Specification |
| --- | --- |
| Free Available Chlorine (FAC) | 70-150 ppm |
| pH | 4.5-6.0 pH Units |

As indicated below in Table 1, all samples were within the FAC specification range of 70 ppm-150 ppm and the pH specification range of 4.5-6.0 for the samples tested.

TABLE 1

Stability Data

| | Test Acceptance Criteria | | FAC | pH |
| --- | --- | --- | --- | --- |
| Data Point | Months @ 40° C. | Equivalent Months @ 22° C. | 70-150 ppm | 4.5-6.0 pH units |
| 1 | 0 | 0.0 | 148.8 | 5.62 |
| 2 | 0.1 | 0.4 | 143.7 | 5.60 |
| 3 | 0.2 | 1.1 | 137.3 | 5.51 |
| 4 | 0.3 | 1.7 | 134.5 | 5.52 |
| 5 | 0.4 | 2.5 | 131.6 | 5.52 |
| 6 | 0.5 | 3.1 | 129.6 | 5.50 |
| 7 | 0.7 | 3.8 | 125.9 | 5.52 |
| 8 | 0.8 | 4.4 | 123.5 | 5.45 |
| 9 | 0.9 | 5.1 | 121.5 | 5.42 |
| 10 | 1.1 | 6.5 | 117 | 5.42 |
| 11 | 1.3 | 7.8 | 114.2 | 5.38 |
| 12 | 1.6 | 9.2 | 109.8 | 5.40 |
| 13 | 1.8 | 10.5 | 108.4 | 5.38 |
| 14 | 2.0 | 11.8 | 101.9 | 5.30 |
| 15 | 2.3 | 13.2 | 101.6 | 5.28 |
| 16 | 2.5 | 14.5 | 98.8 | 5.28 |
| 17 | 2.8 | 16.0 | 95.2 | 5.23 |
| 18 | 3.0 | 17.4 | 93.8 | 5.17 |
| 19 | 3.2 | 18.7 | 89.3 | 5.17 |
| 20 | 3.5 | 20.0 | 86.9 | 5.16 |
| 21 | 3.7 | 21.4 | 84.3 | 5.11 |

Figure 1:
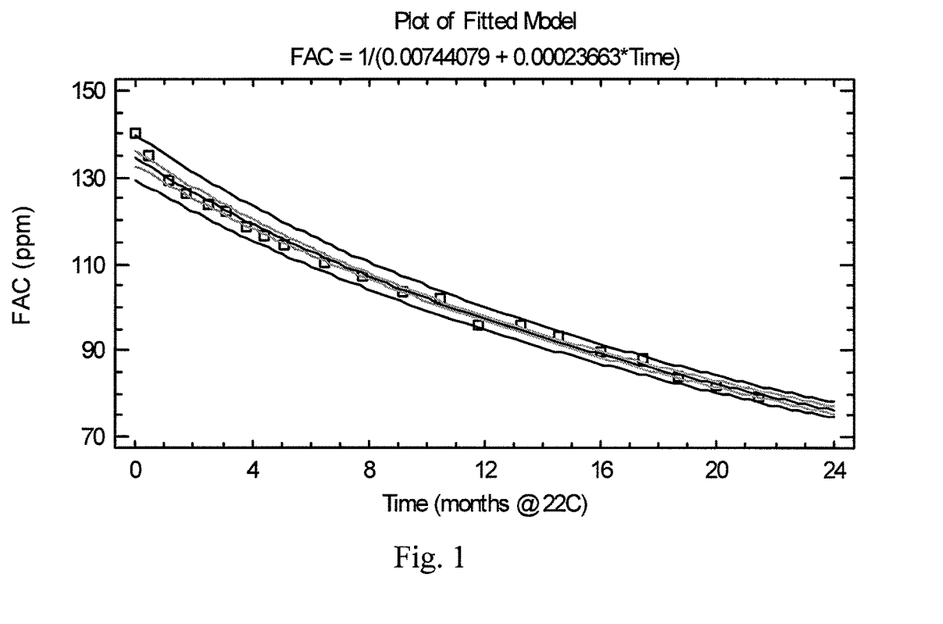
FIG. 1 shows a regression line plot established for the accelerated (40° C.) shelf life Free Available Chlorine (FAC) testing of the low pH antimicrobial solution of the present invention.

Regression lines were established for the accelerated (40° C.) shelf life FAC data (Table 1) using Statgraphics (FIG. 1). Shelf life was set at the point where the lower 95% confidence interval for product FAC manufactured at the lowest end of the manufacturing specification (i.e. worst case scenario) reached 70 ppm. A factor of 5.8 was established to correlate the shelf life obtained at 40° C. to expected shelf life at 22° C. The regression line forecast demonstrates a potential shelf life of well over 28 months.

Example 4

This example demonstrates the increased stability of the low pH antimicrobial solution of the present invention over previously known chlorine-containing solutions of higher pH. More specifically, three solutions were sealed in glass vials and heated to 80° C. to compare degradation. The first had a pH of 7.3, the second had a pH of 5.6 with no buffer, and the third had a pH of 5.6 and contained a phosphate buffer. All three solutions had free available chlorine content of approximately 130 mg/L. The rates of reaction after 87 hours (⅓ degraded) are listed below in Table 2.

TABLE 2

Degradation Rate Based on pH

| Product | Degradation Rate |
| --- | --- |
| pH 7.3 | 0.35 mg/hour |
| pH 5.6 | 0.03 mg/hour |
| pH 5.6 (phosphate buffered) | 0.04 mg/hour |

As shown above in Table 2, the low pH solutions of the present invention (pH of 5.6) demonstrate an approximate 10-fold reduction in degradation rate compared to a solution having a higher pH (pH of 7.3).

Example 5

This example demonstrates the increased stability of the low pH antimicrobial solution of the present invention over previously known chlorine-containing solutions having higher chloride content. The effect of chloride ion at pH 4-6 on the rate of degradation was tested (Table 3). Three solutions were packaged in 8 oz HDPE bottles with flip tops and stored at 40° C.

TABLE 3

Degradation Rate Based on Chloride Ion

| Chloride Content | Degradation Rate |
| --- | --- |
| 0.03% | 0.1 mg/day |
| 0.5% | 1.0 mg/day |
| 1.0% | 6.1 mg/day |

As can be seen in Table 3, increases in chloride content significantly increase degradation rates. Thus, the solutions of the present invention (chloride content of 0.03%) are more stable than typical electrolyzed water products (chloride content of 0.5-1%).

Example 6

Figure 2:
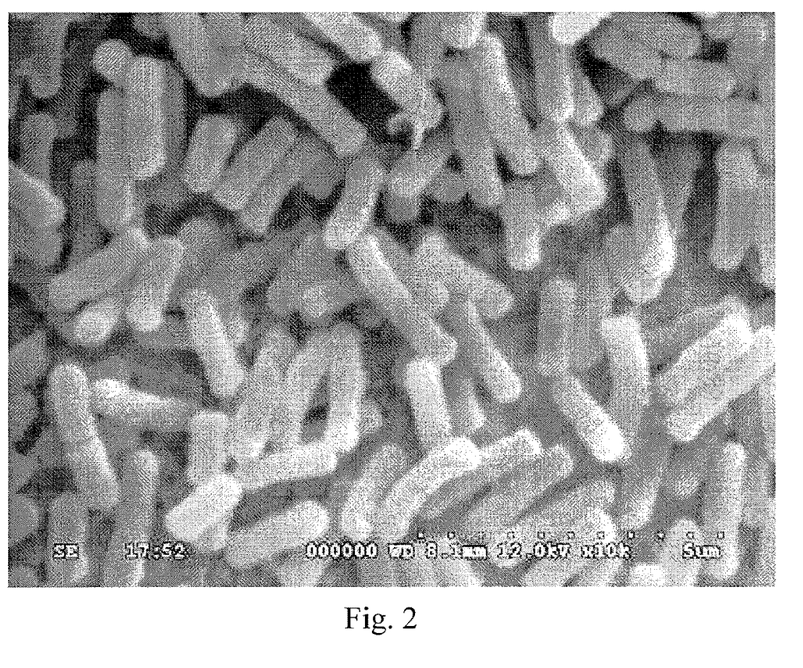
FIG. 2 shows an electron micrograph indicating the cellular topography of a *Pseudomonas aeruginosa* sample following treatment with the low pH antimicrobial solution of the present invention.
Figure 3:
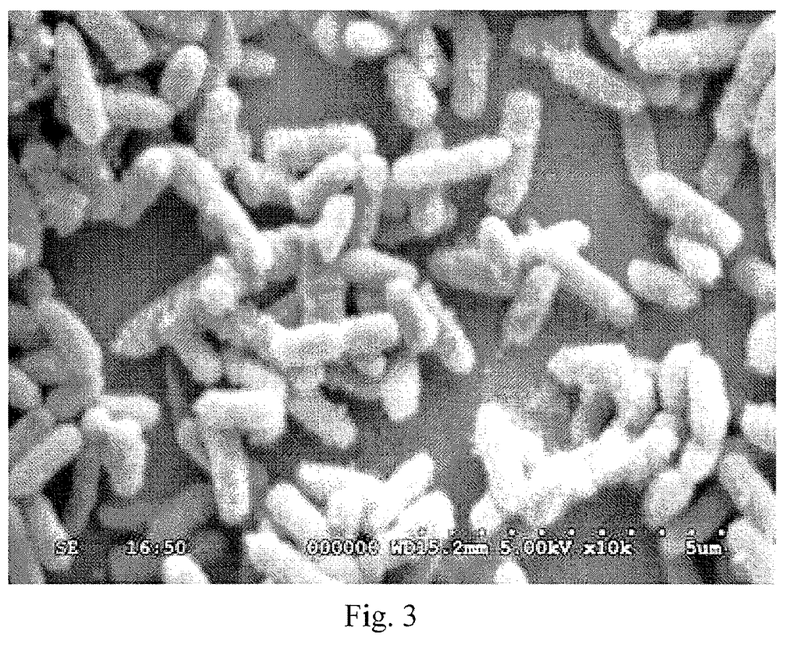
FIG. 3 shows an electron micrograph indicating the cellular topography of a *Pseudomonas aeruginosa* sample following treatment with a prior art solution of pH 7.5.

This example demonstrates the difference in reaction mechanism between the low pH antimicrobial solutions of the present invention and the high chloride/pH solutions of the prior art. In particular, *Pseudomonas aeruginosa* was treated with two solutions (i.e., pH 5 and pH 7.5). The cell samples were evaluated after treatment using electron microscopy. All the bacteria were killed by both solutions. However, the cellular topography was different for the bacteria treated with the pH 5 solution (FIG. 2) than the bacteria treated at pH 7.5 (FIG. 3). Treatment using the pH 5 solution of the present invention provided an electron micrograph showing dead bacterial cells with no change in cellular topography (i.e., no membrane damage). On the other hand, treatment using the prior art solution (i.e., the solution with pH of 7.5) yielded an electron micrograph showing a large quantity of debris from ruptured cells and evidence of membrane damage. This data supports that the HOCl solution of the present invention (pH 5) is reacting through different antimicrobial mechanisms than the prior art HOCl/NaOCl/Cl$_2$O solutions (pH 7.5).

Example 7

This example demonstrates the improved handling of organic load for the low pH antimicrobial solutions of the present invention compared to solutions having higher pH. In particular, two solutions (pH 4.9 and 7.0) were tested against various bacteria in the presence of albumin, an interfering substance that simulates the organic load of a wound and is known to inactivate antimicrobial agents. Serum albumin is a logical choice to represent organic load because it is one of the most abundant proteins in human plasma. The results are shown below in Table 4.

TABLE 4

Level of Albumin Addition Causing Incomplete Kill

|  | pH 4.9 | pH 7.0 |
|---|---|---|
| Escherichia coli | >1250 ppm | 1250 ppm |
| Pseudomonas aeruginosa | >1250 ppm | 1250 ppm |
| Staphylococcus aureus | 1250 ppm | 1000 ppm |

The data indicates that more albumin (i.e., organic load) to inhibit the killing of bacteria at pH 4.9 (present invention) than at pH 7.0 (prior art). Accordingly, the low pH antimicrobial solutions of the present invention will perform better in a wound, where the presence of organic load can inactivate treatment solutions of the prior art.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A low pH antimicrobial solution comprising from 5 mg/L to 200 mg/L hypochlorous acid and water, wherein the solution has a pH of 5.6, a free available chlorine concentration of from 60 mg/L to 150 mg/L, a chloride ion concentration of from 4 mg/L to 75 mg/L, and a buffering agent that is a combination of sodium phosphate monobasic and sodium phosphate dibasic in an amount sufficient to achieve a pH of 5.6, wherein the concentration of free available chlorine is maintained at about 70% or greater from the initial concentration for at least two months after preparation of the low pH antimicrobial solution.

2. The solution of claim 1, wherein the solution is stable for at least six months.

3. The solution of claim 2, wherein the solution is stable for at least one year.

4. The solution of claim 1, wherein the solution comprises hypochlorous acid in an amount from 7 mg/L to 110 mg/L.

5. The solution of claim 1, wherein the solution has a chloride ion content from 4 mg/L to 65 mg/L.

6. The solution of claim 2, wherein the solution is stable for at least three years.

* * * * *